United States Patent
Powers et al.

(10) Patent No.: US 10,487,099 B2
(45) Date of Patent: Nov. 26, 2019

(54) SYNTHESIS OF HYPERVALENT IODINE REAGENTS WITH DIOXYGEN

(71) Applicant: The Texas A&M University System, College Station, TX (US)

(72) Inventors: David Charles Powers, College Station, TX (US); Asim Maity, College Station, TX (US); Sung-Min Hyun, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 16/020,446

(22) Filed: Jun. 27, 2018

(65) Prior Publication Data

US 2019/0002487 A1    Jan. 3, 2019

Related U.S. Application Data

(60) Provisional application No. 62/527,662, filed on Jun. 30, 2017.

(51) Int. Cl.
| | |
|---|---|
| *C07F 13/00* | (2006.01) |
| *C07C 71/00* | (2006.01) |
| *C07C 67/04* | (2006.01) |
| *C07C 67/307* | (2006.01) |
| *C07C 45/39* | (2006.01) |
| *C07C 51/29* | (2006.01) |
| *C07C 303/26* | (2006.01) |
| *C07C 201/12* | (2006.01) |
| *C07C 315/04* | (2006.01) |
| *C07C 381/00* | (2006.01) |
| *C07J 9/00* | (2006.01) |
| *C07D 213/46* | (2006.01) |

(52) U.S. Cl.
CPC ............ *C07F 13/005* (2013.01); *C07C 45/39* (2013.01); *C07C 51/29* (2013.01); *C07C 67/04* (2013.01); *C07C 67/307* (2013.01); *C07C 71/00* (2013.01); *C07C 201/12* (2013.01); *C07C 303/26* (2013.01); *C07C 315/04* (2013.01); *C07C 381/00* (2013.01); *C07D 213/46* (2013.01); *C07J 9/00* (2013.01); *C07C 2601/08* (2017.05); *C07C 2601/14* (2017.05); *C07C 2601/16* (2017.05); *C07C 2601/18* (2017.05); *C07C 2602/10* (2017.05)

(58) Field of Classification Search
CPC .............................. C07C 71/00; C07F 13/005
See application file for complete search history.

(56) References Cited

PUBLICATIONS

Hossain et al., "Unexpected, Drastic Effect of Triflic Acid on Oxidative Diacetoxylation of Iodoarenes by Sodium Perborate. A Facile and Efficient One-Pot Synthesis of (Diacetoxyiodo)arenes." J. Org. Chem. 2005, 70, 6984-6986 (Year: 2005).*
Maity ("Oxidase catalysis via aerobically generated hypervalent iodine intermediates" Nature Chemistry, Oct. 16, 2017, vol. 10, p. 200-204) (Year: 2017).*

(Continued)

*Primary Examiner* — Amy C Bonaparte
(74) *Attorney, Agent, or Firm* — Christenson O'Connor Johnson Kindness PLLC

(57) ABSTRACT

Methods of synthesis of hypervalent iodine reagents and methods for oxidation of organic compounds are disclosed.

25 Claims, 5 Drawing Sheets

(56) References Cited

PUBLICATIONS

Bravo ("Oxidation of Alkyl and Aryl Iodides, Phenylacetaldehyde and Alkenes by Dimethyldioxirane. Reaction Products and Mechanism." Tetrahedron Letters, vol. 36, 1995, p. 6945-6948) (Year: 1995).*
Zhdankin ("Hypervalent iodine(V) reagents in organic synthesis" ARKIVOC, 2006, p. 26-58) (Year: 2006).*
Zhdankin ("Hypevalent iodine(iii) reagents in organic synthesis" ARKIVOC, 2009, p. 1-62) (Year: 2009).*
Maity, A., et al., "Oxidase Catalysis via Aerobically Generated Hypervalent Iodine Intermediates," Nature Chemistry 10(2)200-204, Feb. 2018.
Maity, A., et al., "Oxidation Catalysis by an Aerobically Generated Dess-Martin Periodinane Analogue," Angewandte Chemie International Edition 57(24):7205-7209, Jun. 2018.
Miyamoto, K., et al., "Iodoarene-Catalyzed Oxidative Transformations Using Molecular Oxygen," Chemical Communications 53(70):9781-9784, Aug. 2017.

\* cited by examiner

| Entry | RCHO | Solvent | Initiator | Yield |
|---|---|---|---|---|
| 1 | PhCHO | DCE | none | 0% |
| 2 | $i$-PrCHO | DCE | none | 2% |
| 3 | $n$-PrCHO | DCE | none | 6% |
| 4 | $CH_3CHO$ | DCE | none | 42-91% |
| 5 | $CH_3CHO$ | DCE | $Cu(OAc)_2 \cdot H_2O$ | 48% |
| 6 | $CH_3CHO$ | DCE | $Mn(OAc)_2 \cdot 4H_2O$ | 75% |
| 7 | $CH_3CHO$ | DCE | $CoCl_2 \cdot 6H_2O$ | 99% |
| 8 | $CH_3CHO$ | $CH_3CN$ | $CoCl_2 \cdot 6H_2O$ | 73% |
| 9 | $CH_3CHO$ | AcOH | $CoCl_2 \cdot 6H_2O$ | 98% |
| 10 | $CH_3CHO$ | THF | $CoCl_2 \cdot 6H_2O$ | 0% |

*a* These reactions with carried out in 1,2-dichloroethane (DCE) as reaction solvent.

SYNTHESIS OF HYPERVALENT IODINE REAGENTS WITH DIOXYGEN

CROSS-REFERENCES TO RELATED APPLICATIONS

This application claims the benefit of U.S. Provisional Application No. 62/527,662, filed Jun. 30, 2017, the disclosure of which is expressly incorporated herein by reference in its entirety.

BACKGROUND OF THE INVENTION

Hypervalent iodine compounds are generated by oxidation of organic iodides and feature 3-centered, 4-electron (3c-4e) bonding at iodine. Hypervalent iodine reagents are broadly useful chemical oxidants in organic synthesis, with demonstrated applications in diverse reactions such as substrate hydroxylation and amination chemistry, olefin functionalization, and oxidative dearomatization. The broad utility of these reagents derives from facile ligand exchange chemistry at iodine, which allows use of hypervalent iodine reagents to accomplish a diverse set of group-transfer and substrate-oxidation reactions. Liabilities of hypervalent iodine reagents include 1) the need to stoichiometric quantities and 2) the common use of wasteful metal-based oxidants, such as $KMnO_4$, $NaIO_4$, and oxone, or organic peracids, such as mCPBA, in the synthesis of these chemicals. A need exists for a cost effective, efficient method of synthesis of these useful reagents for organic synthesis.

Dioxygen ($O_2$) is an attractive oxidant for synthetic chemistry because it displays a large reduction potential, is readily available, and is environmentally benign. Selective and efficient utilization of $O_2$ in synthesis, however, is challenging because the triplet ground state of $O_2$ gives rise to poorly selective radical chemistry. In addition, one must manage the disparate electron inventories of 4-electron reduction of $O_2$ with the 2-electron oxidations common in synthesis. Development of new chemical strategies to couple $O_2$ reduction directly to substrate oxidation would underpin development of more sustainable synthetic methods.

The present invention fulfills these unmet needs by providing a method of aerobic oxidation of aryl iodides to aryl hypervalent iodine reagents and by providing a broad access to new oxidation methods of organic substrates directly utilizing dioxygen.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

SUMMARY OF THE INVENTION

In one aspect, provided herein is a method of synthesis of an aryl hypervalent iodine reagent, comprising contacting an aryl iodide in a suitable solvent with an aliphatic aldehyde and a source of dioxygen, thereby forming the aryl hypervalent iodine reagent.

In some embodiments, the aryl hypervalent iodine reagent is an aryl iodine I(III) or I(V) aryl hypervalent iodine reagent having the structure of Formula (I), Formula (II), Formula (III), Formula (IV), or Formula (V):

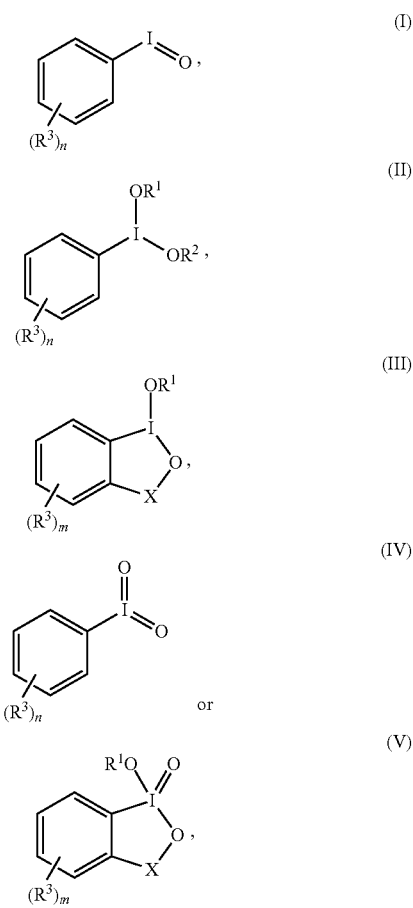

$R^2$ is H, optionally substituted $C_1$-$C_6$ alkyl, Ac, or Ts;

$R^3$, independently at each occasion, is H, optionally substituted $C_1$-$C_6$ alkyl, optionally substituted $C_1$-$C_6$ alkoxy, COOH, H, Cl, Br, $CF_3$, $NO_2$, $SO_2R^4$, optionally substituted aryl, optionally substituted heteroaryl, or two $R^3$ at adjacent carbon atoms together with the atoms at which they are attached form an optionally substituted 5 or 6-membered aliphatic or aromatic cycle;

$R^4$ is optionally substituted $C_1$-$C_6$ alkyl, optionally substituted aryl, optionally substituted heteroaryl;

X is C(O), $C(CH_3)_2$, $C(CF_3)_2$, or I(OAc);

n is 0, 1, 2, 3, 4, or 5; and m is 0, 1, 2, 3, or 4.

In another aspect, a method of oxidizing an organic compound is provided, the method comprising contacting the compound in a suitable solvent with aryl iodide, an aliphatic aldehyde, and dioxygen, thereby oxidizing the organic compound.

In another aspect, a method of oxidizing a C—H bond in an organic compound is provided, the method comprising contacting the compound in a suitable solvent with an aryl iodide, an aliphatic aldehyde, and dioxygen, thereby oxidizing the C—H bond.

In some embodiments of the oxidation methods disclosed herein, the aryl iodide is used in less than stoichiometric amounts, for example, the molar ratio of the organic compound to aryl iodide is about 3:1, about 5:1, about 10:1, about 15:1, or about 20:1. In some embodiments, the method is performed in the presence of p-TsOH or [TBA]Br. In some embodiments, the source of dioxygen is air or dioxygen gas. In some embodiments, the method is performed in one pot.

DETAILED DESCRIPTION

The invention is based on the surprising discovery that aldehyde autoxidation could be diverted to generate hypervalent iodine reagents. Specifically, the synthesis of aryl hypervalent iodine reagents can be readily accomplished using dioxygen ($O_2$) by intercepting intermediates of aldehyde autoxidation reactions. This chemistry is readily applicable to a diverse set of organic oxidation reactions.

Figure 1:
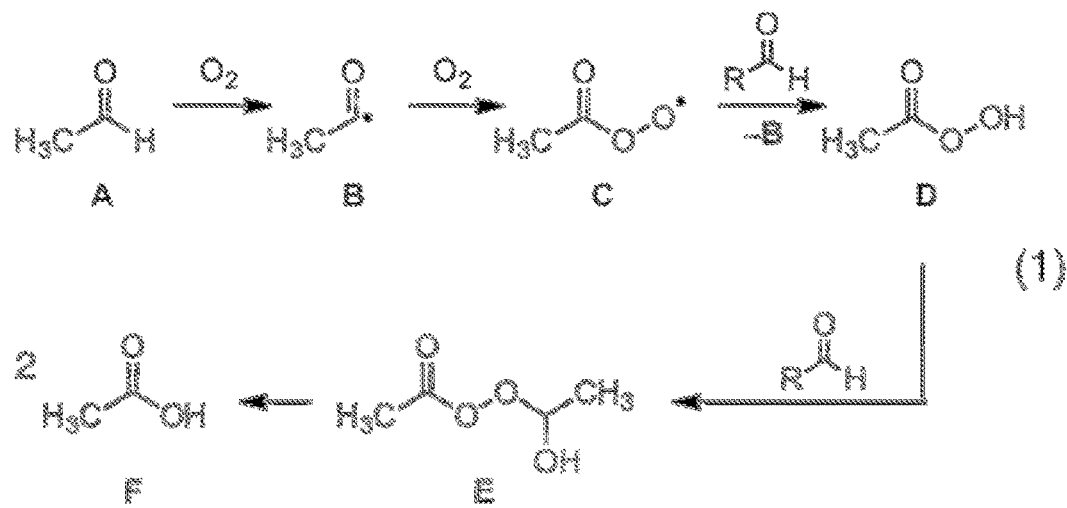
FIG. 1 depicts radical chain mechanism for aldehyde autoxidation which involves hydrogen-atom abstraction from an aldehyde (A) to generate an acyl radical (B), reaction of B with $O_2$ to generate acyl peroxy radical C, and HAA to generate an equivalent of peracid (D) and the acyl radical chain carrier B.

The conversion of benzaldehyde to benzoic acid under the action of $O_2$ was first noted by Wöhler and Liebig in 1832. In 1900, Baeyer and Villiger isolated perbenzoic acid from this reaction and proposed that formation of benzoic acid was accomplished by the oxidation of benzaldehyde with perbenzoic acid via the eponymous Baeyer-Villiger reaction. In 1927, Bäckström advanced the now-accepted radical chain mechanism for aldehyde autoxidation, which involves hydrogen-atom abstraction from an aldehyde to generate an acyl radical (B), reaction of B with $O_2$ to generate acyl peroxy radical C, and HAA to generate an equivalent of peracid (D) and the acyl radical chain carrier B, as shown in FIG. 1.

Radical-chain autoxidation chemistry underlies large-scale industrial oxidation reactions, such as the conversion of p-xylene to terphthalic acid and the oxidation of cumene to phenol and acetone. Recently, aldehyde autoxidation intermediates have been utilized in the development of synthetic methods for olefin addition and oxidation. The inventors reasoned that if the intermediates of aldehyde autoxidation could be diverted to generate hypervalent iodine reagents, the utility of autoxidation as a mechanism for aerobic oxidation would be greatly expanded beyond substrates that readily participate in radical chemistry. Here, in one aspect, the inventors disclose the synthesis of hypervalent iodine reagents with $O_2$, which are accessed by intercepting intermediates of aldehyde autoxidation reactions and the application of this chemistry to a diverse set of organic oxidation reactions. The inventors initiated the investigation of aerobic oxidation of aryl iodides by examining the viability of oxidation of PhI with $O_2$ in the presence of a variety of simple aldehydes in 1,2-dichloroethane (DCE) at 23° C. (FIG. 2; for optimization experiments, yields were determined by $^1$H NMR).

Figure 2:
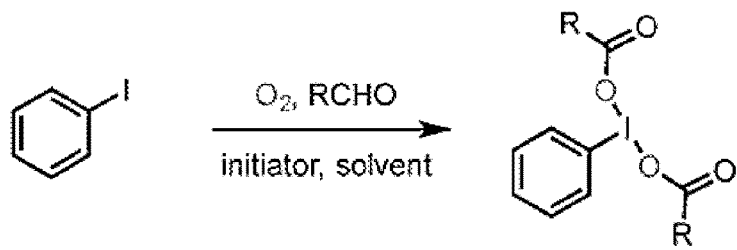
FIG. 2 illustrates optimization of aerobic oxidation of iodobenzene to generate iodobenzene diacetate.
Figure 3:
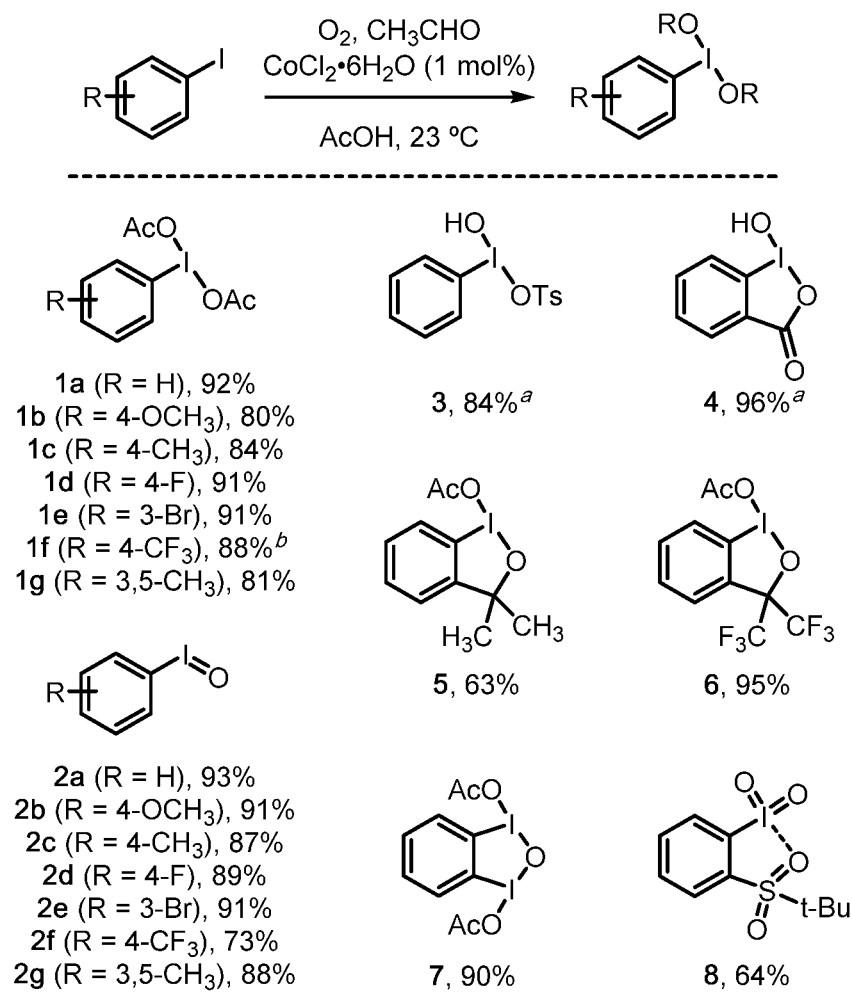
FIG. 3 demonstrates that aerobic oxidation of aryl iodides provides direct access to a family of common oxygenated hypervalent iodine reagents. One-pot ligand exchange allows for the synthesis of hypervalent iodine reagents that are common in organic oxidation chemistry.
Figure 4:
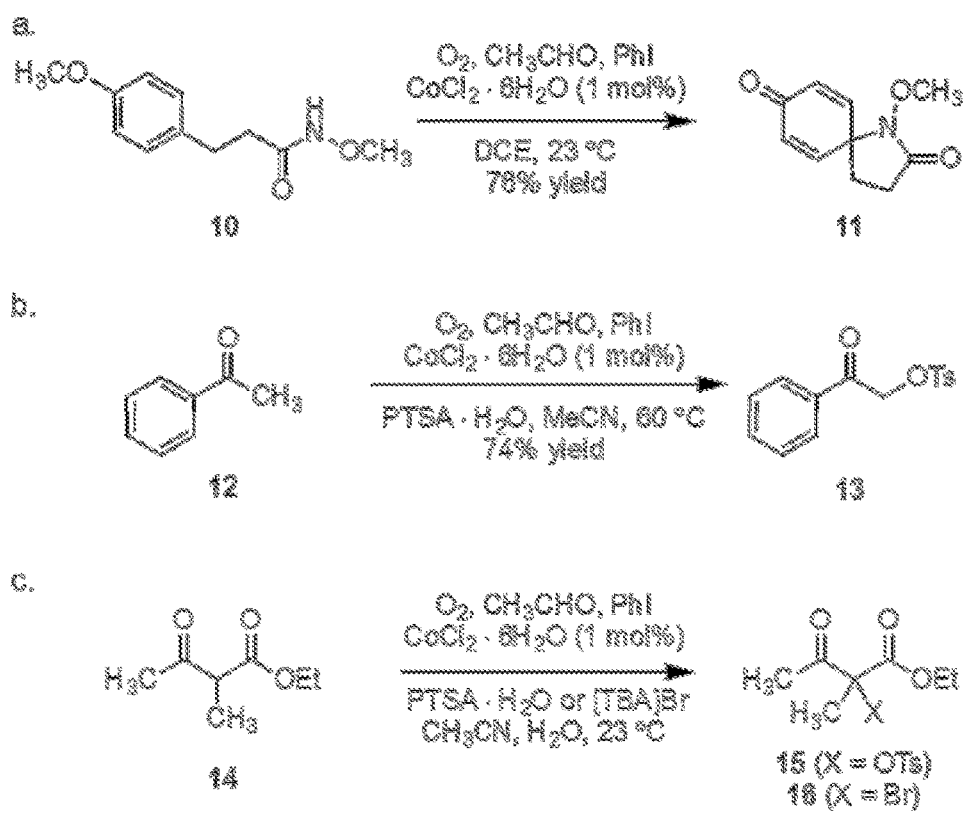
FIG. 4 shows that PhI-catalyzed aerobic oxidation supports a) oxidative dearomatization, b) α-oxygenation and halogenation of ketones, and c) oxidation of β-ketoesters.
Figure 5:
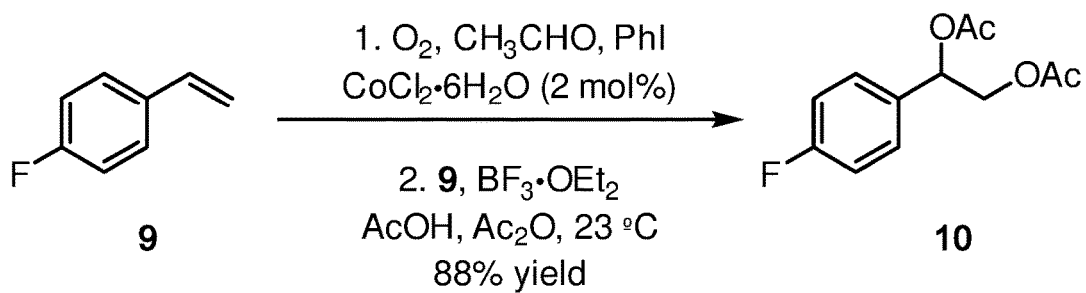
FIG. 5 shows that one-pot aerobic oxidation can be applied to oxidation reactions that contain radical inhibitors, such as phenols and styrenes.

The inventors discovered that while benzaldehyde was ineffective in promoting oxidation of iodobenzene (FIG. 2, Entry 1), isobutyraldehyde and butyraldehyde led to the observation of 2% and 6% yield of I(III), respectively (FIG. 2, Entries 2 and 3). Use of acetaldehyde afforded $PhI(OAc)_2$ in 42-91% yield (yields obtained from five identical reactions, FIG. 2, Entry 4). The variability of oxidation efficiency was likely due to inconsistent initiation of radical autoxidation chemistry. Addition of various metal salts (1 mol %) that have been demonstrated to be competent autoxidation initiators (FIG. 2, entries 5-7) led to identification of $CoCl_2 \cdot 6H_2O$ as a highly effective and reproducible initiator, leading to $PhI(OAc)_2$ in 99% yield. Using $CoCl_2 \cdot 6H_2O$ as catalyst, aryl iodide oxidation can be accomplished in 63% yield using air in place of $O_2$. The developed aerobic oxidation is compatible with a broad range of organic solvents; in addition to DCE, high yields are obtained in coordinating solvents, such as $CH_3CN$ (FIG. 2, Entry 8), and protic solvents, such as AcOH (FIG. 2, Entry 9). In contrast, oxidation of PhI is not accomplished in THF, which is presumably due to the presence of weak C—H bonds that inhibit radical chain aldehyde oxidation (vide infra).

In some embodiments, the presently disclosed methods are applicable to synthesis of an aryl hypervalent iodine reagent by contacting an aryl iodide in a suitable solvent with an aliphatic aldehyde and a source of dioxygen, thereby forming the aryl hypervalent iodine reagent. The aryl hypervalent iodine reagent is aryl iodine I(III) or I(V) reagent.

A variety of I(III) or I(V) reagents can be generated using the provided aerobic oxidation conditions.

In some embodiments, the aryl hypervalent iodine reagent is a aryl iodine I(III) reagent. In some embodiments, the aryl hypervalent iodine reagent has the structure of Formula (I), Formula (II), or Formula (III):

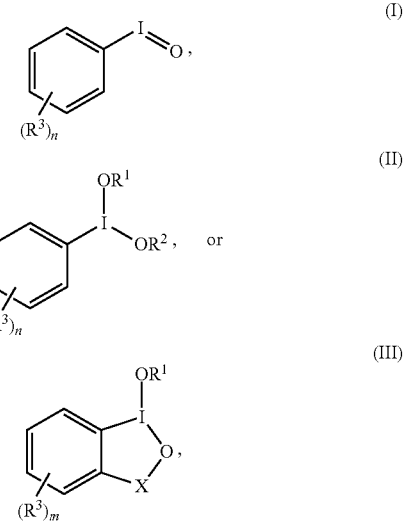

or a salt or a tautomer thereof, wherein:

$R^1$ is H, Ts, or Ac;

$R^2$ is H, optionally substituted $C_1$-$C_6$ alkyl, Ac, or Ts;

$R^3$, independently at each occasion, is H, optionally substituted $C_1$-$C_6$ alkyl, optionally substituted $C_1$-$C_6$ alkoxy, COOH, H, Cl, Br, $CF_3$, $NO_2$, $SO_2R^4$, optionally substituted aryl, optionally substituted heteroaryl, or two $R^3$ at adjacent carbon atoms together with the atoms at which they are attached form an optionally substituted 5 or 6-membered aliphatic or aromatic cycle;

$R^4$ is optionally substituted $C_1$-$C_6$ alkyl, optionally substituted aryl, optionally substituted heteroaryl;

X is C(O), $C(CH_3)_2$, $C(CF_3)_2$, or I(OAc);

n is 0, 1, 2, 3, 4, or 5; and m is 0, 1, 2, 3, or 4.

In certain embodiments, the aryl hypervalent iodine reagent has the structure of Formulae 1a, 1b, 1c, 1d, 1e, 1f, 1g, 2a, 2b, 2c, 2d, 2d, 2e, 2f, 2g, 3, 4, 5, 6, or 7:

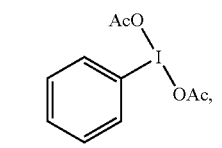
1a

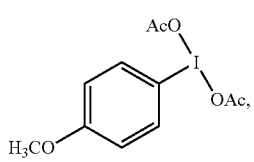
1b

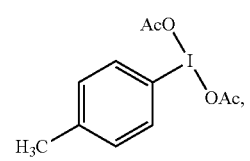
1c

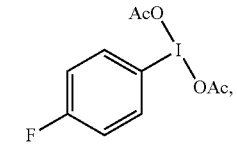
1d

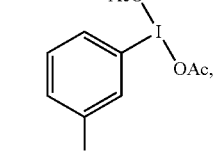
1e

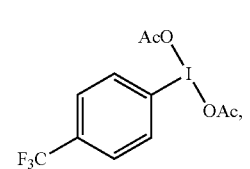
1f

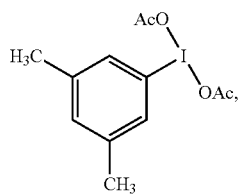
1g

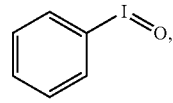
2a

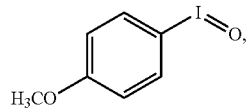
2b

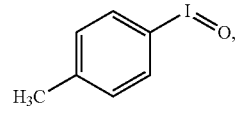
2c

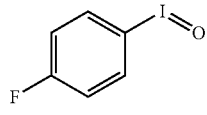
2d

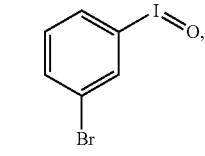
2e

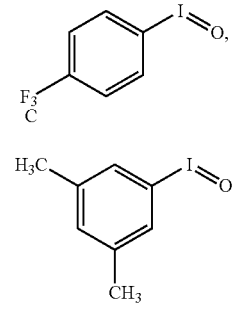
2f

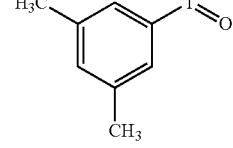
2g

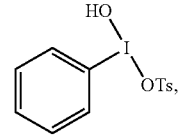
3

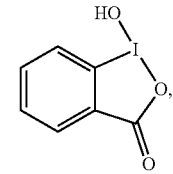
4

-continued

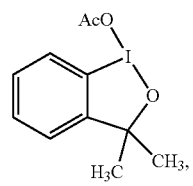

5

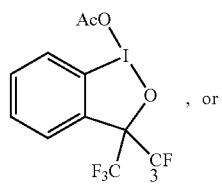, or

6

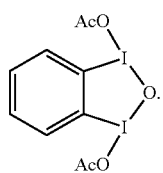

7

In some instances, aryl iodide oxidation is tolerant to para-substitution on the aromatic ring, which provides a handle to tune the activity and aggregation state of resulting I(III) reagent. Addition of TsOH to the oxidation of PhI affords the acid-activated iodosylbenzene reagent 3 in 84% yield. Aldehyde-promoted oxidation of 2-iodobenzoic acid, 2-(2-iodophenyl)propan-2-ol, and 1,1,1,3,3,3-hexafluoro-2-(2-iodophenyl)propan-2-ol, each affords I(III) products (Compounds of Formula 4, 5, and 6, respectively) in which the ortho-substituent chelates to the oxidized iodine center. These chelated hypervalent iodine reagents are useful because they display enhanced solubility. Finally, oxidation of 1,2-diiodobenzene affords bis-iodine(III) compound of Formula 7 in 24% yield, which is similar to the yield for similar oxidation with AcOOH. Unlike the aforementioned oxidation reactions, which generate I(III) derivatives in high yield, oxidation of 2-tert-butylsulfonyliodobenzene affords I(V) derivative of Formula 8.

In some embodiments, the aryl hypervalent iodine reagent is an aryl I(V) reagent. In some embodiments, the aryl hypervalent iodine reagent has the structure of Formula (IV) or Formula (V):

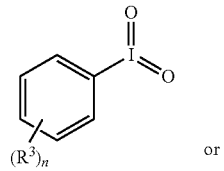

(IV)

or

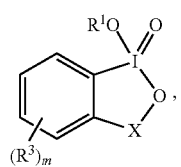

(III)

or a salt or a tautomer thereof, wherein:

$R^1$ is H, Ts, or Ac;

$R^3$, independently at each occasion, is H, optionally substituted $C_1$-$C_6$ alkyl, optionally substituted $C_1$-$C_6$ alkoxy, H, Cl, Br, $CF_3$, $NO_2$, $SO_2R^4$, optionally substituted aryl, optionally substituted heteroaryl, or two $R^3$ at adjacent carbon atoms together with the atoms at which they are attached form an optionally substituted 5 or 6-membered aliphatic or aromatic cycle;

$R^4$ is optionally substituted $C_1$-$C_6$ alkyl, optionally substituted aryl, optionally substituted heteroaryl;

X is $C(CH_3)_2$, $C(CF_3)_2$, or I(OAc).

n is 0, 1, 2, 3, 4, or 5; and m is 0, 1, 2, 3, or 4.

In particular embodiments, the aryl hypervalent iodine reagent has the structure of Formulae 21, 22, 24, 25, 26, 27, 28, 29, 30, or 31:

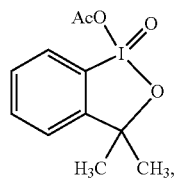

21

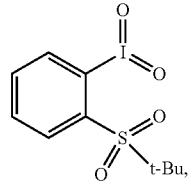

22

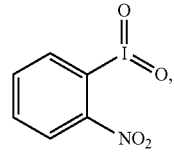

24

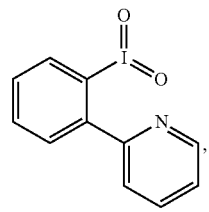

25

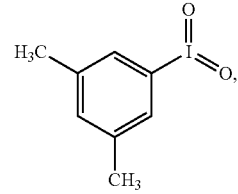

26

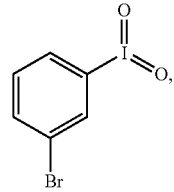

27

-continued

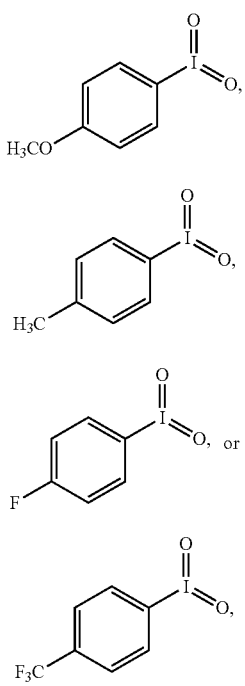

or a salt or a tautomer thereof.

In some instances, the aliphatic aldehyde of the methods of synthesis of an aryl hypervalent iodine reagent has a formula $R^1CHO$, wherein $R^1$ is a $C_1$-$C_6$ alkyl. In certain embodiments, the aldehyde is acetaldehyde, propionaldehyde, or butyraldehyde. An example of a particularly useful aliphatic aldehyde is acetaldehyde.

A variety of suitable solvents can be used in the present methods, including coordinating solvents, non-coordinating solvents, polar aprotic solvents, or protic solvents. Particularly suitable solvents include 1,2-dichloroethane, acetic acid, and acetonitrile.

In some embodiments, the methods of synthesis of an aryl hypervalent iodine reagent are performed in the presence of an autooxidation initiator, such as but not limited to $CoCl_2.6H_2O$, $Cu(OAc)_2.H_2O$, and $Mn(OAc)_2 4H_2O$.

The dioxygen gas employed in the present methods can be in any suitable form or come from any suitable source. In some embodiments, the dioxygen gas is in the form of a mixture with at least one other gas. A particularly useful $O_2$ source is air. In some embodiments, the methods are performed at an atmospheric pressure. In some embodiments, the methods are performed at ambient temperatures, for example, at a temperature between about 20° C. and about 30° C.

In another aspect, a method of oxidizing an organic compound is provided, the method comprising contacting the compound in a suitable solvent with aryl iodide, an aliphatic aldehyde, and dioxygen, thereby oxidizing the organic compound. In some embodiments, the method of oxidizing an organic compound involves oxidizing a C—H bond in an organic compound. In certain embodiments, the aryl hypervalent iodine reagents are generated in situ. In some embodiments, the generation of an aryl hypervalent iodine reagents and substrate oxidation are performed in one pot. In some instances, the aryl iodide is used in less than stoichiometric amount, for instance, in a catalytic amount.

The methods of oxidation of organic compounds described herein have broad synthetic utility, for instance, in oxidative dearomatization, carbonyl α-oxidation reactions, and olefin difunctionalization, which are common synthetic applications of hypervalent iodine reagents. For example, oxidative de-aromatization of Weinreb amide 10 using the $CH_3CHO$, $O_2$, and $CoCl_2.6H_2O$ conditions affords lactam 11 in 76% yield. α-Oxidation of carbonyl compounds is also readily coupled to $O_2$ as a terminal oxidant using the oxidation methods disclosed herein.

In some embodiments, the methods disclosed herein can be used for oxidative functionalization, e.g., bromination or tosylation, of organic compounds. For example, acetophenone undergoes α-tosylation to afford oxygenated compound 13 in 73% yield in the presence of $O_2$, acetaldehyde, PhI, and TsOH. Similarly, β-ketoester Compound 14 participates in α-tosylation to afford Compound 15 when subjected to the standard autoxidation conditions with the addition of TsOH. Importantly, the addition [TBA]Br results in the formation of α-brominated Compound 16. The facility of introduction of non-oxygen functionality in these reactions highlights the utility of hypervalent iodine reagents to promote a wide variety of oxidative functionalization reactions that are not possible with AcOOH alone. The ability to accomplish ligand exchange chemistry at hypervalent iodine compounds underpins the ability to extend the developed aerobic oxidation chemistry to aerobic bromination.

In some instances, application of the aerobic oxidation chemistry methods of the invention to substrates that contain radical inhibiting functionality, such as phenols and olefins, is challenging. Attempts to accomplish either oxidative lactonization of Compound 17 or 1,2-difunctionalization of styrene derivatives (i.e., Compound 19) under standard aerobic oxidation conditions afforded only trace product formation. In both cases, aldehyde autoxidation is inhibited. In contrast, if the aerobic oxidation is accomplished and the substrate in question (i.e., a substrate that has a radical-inhibiting functionality) added subsequently, efficient lactonization and olefin functionalization reactions are observed. While not catalytic in PhI, these reactions demonstrate the viability of coupling both these reactions to $O_2$ as the terminal oxidant.

Figure 6A:
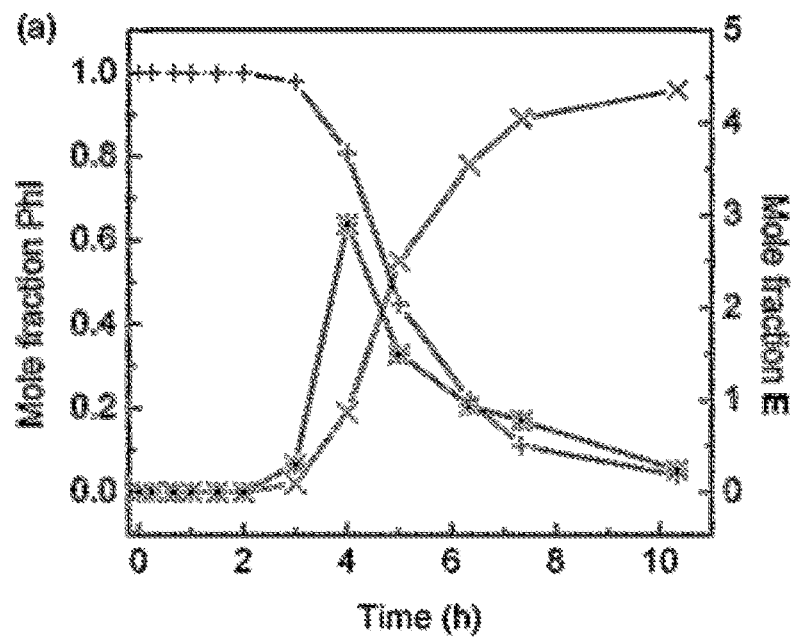
FIGS. 6A and 6B show mole fractions of PhI (+), PhI $(OAc)_2$ (x), and 1-hydroxyethyl ethaneperoxoate E, (*) as a function of time for oxidation of PhI in $CDCl_3$ with acetaldehyde at 23° C. (A) without $CoCl_2.6H_2O$ and (B) with $CoCl_2.6H_2O$.
Figure 6B:
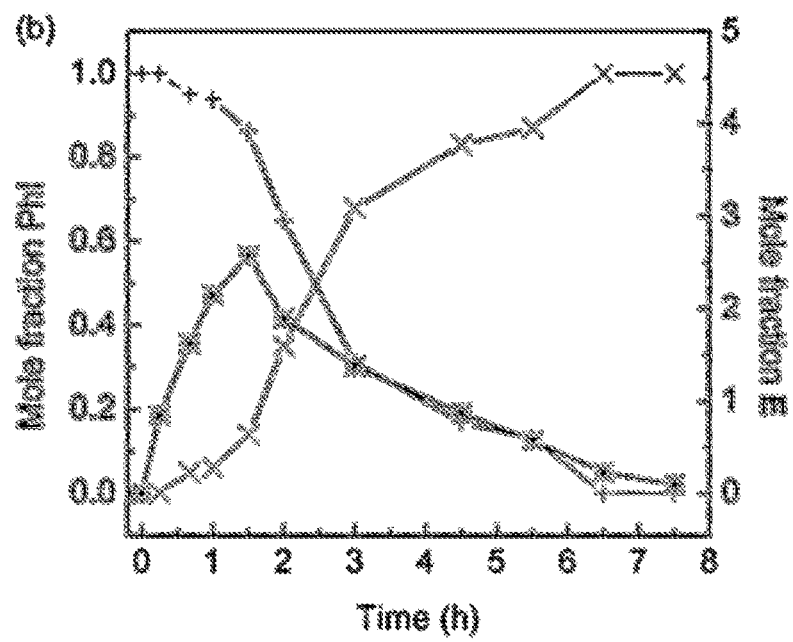

Without wishing to be bound by theory, the aerobic oxidation of aryl iodides disclosed herein was predicated on the hypothesis that strongly oxidizing intermediates in aldehyde autoxidation chemistry could be coopted for the synthesis of iodinanes. Consistent with this hypothesis, the use of reaction solvents with weak C—H bonds (i.e., THF) or the addition of 2,6-di-tert-butyl-4-methylphenol (BHT), a common radical inhibitor, suppressed the formation of hypervalent iodine products. In addition, the reaction kinetics if PhI oxidation was followed by $^1H$ NMR spectroscopy. Consistent with the observation of highly variable yields in the absence of radical initiators, in the absence of $Co_2Cl_2.6H_2O$, substantial induction periods of differing lengths of time are observed. In the presence of $Co_2Cl_2.6H_2O$, the induction period for evolution of PhI $(OAc)_2$ is substantially shortened (FIGS. 6A and 6B). Notably, when following aerobic oxidation by $^1H$ NMR, the inventors observed the initial evolution of a quartet at 5.41 ppm, a singlet at 2.01 ppm, and a doublet at 1.35 ppm, which integrate as a 1:3:3 ratio. These signals are attributable to intermediate E (FIG. 1), which is the adduct of a molecule of aerobically generated AcOOH and a molecule of $CH_3CHO$. This structure assignment was confirmed by high-resolution mass spectrometry of the oxidation reaction which reveals the presence of a signal at m/z=143.0318

Figure 7A:
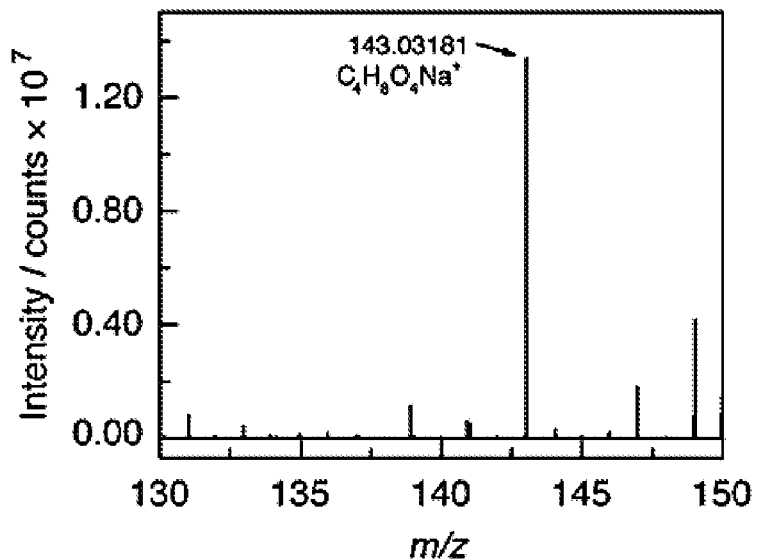
FIGS. 7A and 7B show mass spectra of reaction mixtures demonstrating presence of 1-hydroxyethyl ethaneperoxoate.
Figure 7B:
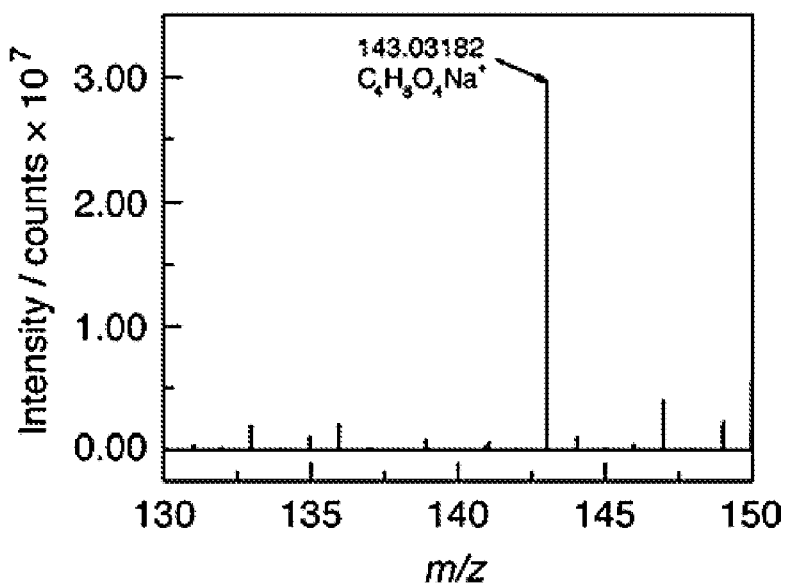

(M+Na+ for E, FIGS. 7A and 7B). At this time, no differentiation between aerobically generated AcOOH and E as the oxidant that directly engages with ArI to generate the observed hypervalent iodine reagents can be made. Observation of E confirms that aldehyde autoxidation is operative during the aerobic ArI oxidation chemistry.

While illustrative embodiments have been illustrated and described, it will be appreciated that various changes can be made therein without departing from the spirit and scope of the invention.

EXAMPLES

A. General Considerations

A1. Materials

All chemicals and solvents were obtained as ACS reagent grade and used as received. Iodobenzene and styrene were obtained from Beantown Chemical. Acetaldehyde, 2-iodonitrobenzene, (4-methoxy)-phenyl propanoic acid and p-toluenesulfonic acid monohydrate were obtained from Alfa Aesar. Sodium hydroxide and ethyl acetate were obtained from EMD Millipore. 2-iodobenzoic acid, 4-iodoanisole, 4-iodotoluene, 3bromoiodobenzene, 2,5-dimethyliodobenzene, 1,2-diiodobenzene, butylated hydroxytoluene, acetophenone, 2-methylethyl acetoacetate, N-tert-butyl-α-phenylnitrone, 1,2-dichloroethane, benzoic acid, 4-fluorostyrene, borontrifluoride diethyletherate, diethylether, methanol, THF, hexanes, acetic acid, and acetic anhydride were obtained from Sigma-Aldrich. Tetrabutylammonium bromide was purchased from Chem-Impex Intl Inc. Silica gel (0.060-0.200 mm, 60 Å for column chromatography) was obtained from Acros Organics. $CH_2Cl_2$, acetonitrile, and toluene were obtained from Fisher Scientific. O-Methylhydroxylamine hydrochloride, butyraldehyde, and isobutyraldehyde were obtained from TCI. NMR solvents were purchased from Cambridge Isotope Laboratories and were used as received. $O_2$ (99.6%) was obtained from Conroe Welding Supply. Substituted phenyl ethyl alcohols were prepared from the corresponding ketones by $NaBH_4$ reduction according to literature methods. All reactions were carried out under ambient atmosphere unless otherwise noted.

A2. Characterization Details

NMR spectra were recorded on Mercury 300 FT NMR for $^1H$ acquisitions and were referenced against solvent signals: $CDCl_3$ (7.26 ppm, H; 77.16 ppm, $^{13}C$), $D_2O$ (4.79 ppm, $^1H$), and DMSO-$d_6$ (2.50 ppm, $^1H$). H NMR data are reported as follows: chemical shift (δ, ppm), (multiplicity: s (singlet), d (doublet), t (triplet), m (multiplet), br (broad), integration). Mass spectrum was recorded on Q Exactive™ Focus Hybrid Quadrupole-Orbitrap™ Mass Spectrometer from Thermo-Fisher Scientific. GC experiments were conducted on TherrmoFisher Scientific Trace 1310 Gas Chromatograph. Melting points (mp) were measured using MelTemp II from Laboratory Devices Inc. For reports of mp, decomp stands for decomposition and expl stands for explosion

B1. Synthesis of Aryl Hypervalent Iodine (III) Reagents

Synthesis of Iodobenzene Diacetate (1a) and Iodosylbenzene (2a)

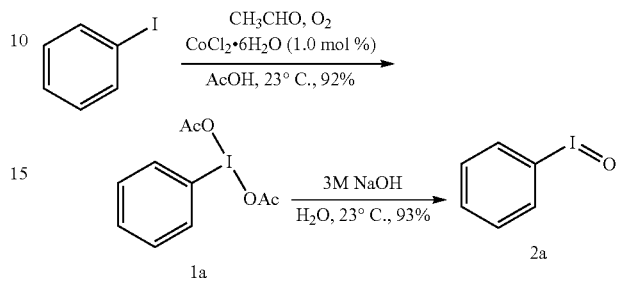

A 20-mL scintillation vial was charged with glacial AcOH (2 mL), iodobenzene (82.2 mg, 0.401 mmol, 1.00 equiv) and $CoCl_2·6H_2O$ (0.9 mg, 0.004 mmol, 1 mol %) and was fitted with a rubber septum. The reaction vessel was purged with $O_2$ for 5 min before acetaldehyde (224 μL, 4.07 mmol, 10.2 equiv) was added in one portion. The reaction mixture was stirred under 1 atm $O_2$, delivered by inflated balloon, at 23° C. for 5 h. The solvent was removed in vacuo and residue was dissolved in $CH_2Cl_2$. The organic layer was washed with distilled water and extracted with $CH_2Cl_2$ (3×7 mL). The organic layer was dried over $MgSO_4$ and solvent was removed in vacuo to afford 119 mg of iodobenzene diacetate (1a) as white solid (92% yield). Characterization of 1a: $^1H$ NMR (δ, 23° C., $CDCl_3$): 8.09 (d, J=7.3 Hz, 2H), 7.63-7.47 (m, 3H), 2.01 (s, 6H). $^{13}C$ NMR (δ, 23° C., $CDCl_3$): 176.5, 135.0, 131.8, 131.0, 121.7, 20.5. The obtained spectral data are in good agreement with those reported in literature.

A 20-mL scintillation vial was charged with iodobenzene diacetate (1a) (97.1 mg, 0.301 mmol, 1.00 equiv) and 3 M NaOH (5 mL). The reaction mixture was stirred for 3 h at 23° C. The resulting suspension was then filtered to afford 62 mg of iodosylbenzene (2a) as yellow solid (93% yield). Characterization of 2a: $^1H$ NMR (δ, 23° C., $CD_3OD$): 8.04 (dd, J=7.5, 2.1 Hz, 2H), 7.60-7.56 (m, 3H). $^{13}C$ NMR data have not been collected due to poor solubility of 2a. HRMS (ESI+): Calcd. for $C_6H_6IO$ [M+H]+ m/z 220.9463. The recorded spectral data are in good agreement with those reported in literature.

Synthesis of 4-methoxy-iodobenzene diacetate (1b) and 4-methoxy iodosylbenzene (2b)

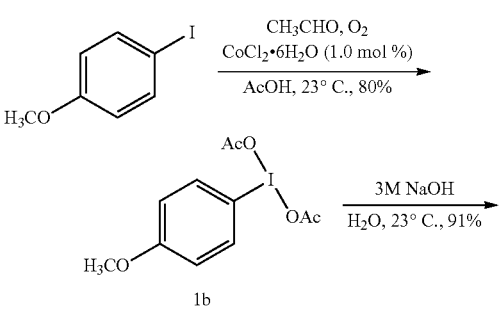

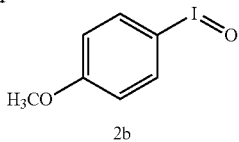

2b

A 20-mL scintillation vial was charged with glacial AcOH (2 mL), 4-methoxy-iodobenzene (94.3 mg, 0.402 mmol, 1.00 eq.) and $CoCl_2 \cdot 6H_2O$ (0.9 mg, 0.004 mmol, 1 mol %) and was fitted with a rubber septum. The reaction vessel was purged with $O_2$ for 5 min before acetaldehyde (224 μL, 4.07 mmol, 10.1 eq.) was added in one portion. The reaction mixture was stirred under 1 atm $O_2$, delivered by inflated balloon, at 23° C. for 10 h. The solvent was removed in vacuo and residue was dissolved in $CH_2Cl_2$. The organic layer was washed with distilled water and extracted with $CH_2Cl_2$ (3×7 mL). The organic layer was dried over $MgSO_4$ and solvent was removed in vacuo to afford 113 mg of 4-methoxy-iodobenzene diacetate (1b) as white solid (80% yield). Characterization of 1b: $^1$H NMR (δ, 23° C., $CDCl_3$): 8.01 (d, J=9.0 Hz, 2H), 6.96 (d, J=9.1 Hz, 2H), 3.86 (s, 3H), 1.99 (s, 6H). $^{13}$C NMR (δ, 23° C., $CDCl_3$): 176.4, 162.1, 137.1, 116.6, 111.6, 55.6, 20.4. The obtained spectral data are in good agreement with those reported in literature.

A 20-mL scintillation vial was charged with 4-methoxy-iodobenzene diacetate (1b) (104 mg, 0.295 mmol, 1.00 eq.) and 3 M NaOH (5 mL). The reaction mixture was stirred for 3 h at 23° C. The resulting suspension was then filtered to afford 67 mg of 4-methoxy iodosylbenzene (2b) as yellow solid (91% yield). Characterization of 2b: $^1$H NMR (δ, 23° C., $CD_3OD$): 7.95 (d, J=9.1 Hz, 2H), 7.18 (d, J=9.1 Hz, 2H), 3.89 (s, 3H). $^{13}$C NMR data have not been collected due to poor solubility of 2b. HRMS (ESI$^+$): Calcd. for $C_7H_7INaO_4$ [M+Na]$^+$ m/z 272.9388. Found: 272.9373.

Synthesis of 4-methyl-iodobenzene diacetate (1c) and 4-methyl iodosylbenzene (2c)

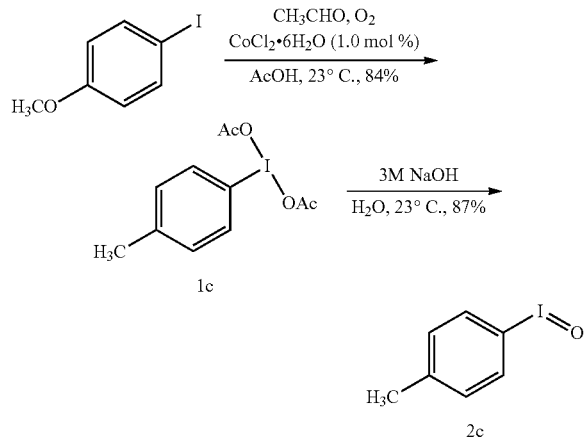

A 20-mL scintillation vial was charged with glacial AcOH (2 mL), 4-methyl-iodobenzene (87.2 mg, 0.399 mmol, 1.00 eq.) and $CoCl_2 \cdot 6H_2O$ (0.9 mg, 0.004 mmol, 1 mol %) and was fitted with a rubber septum. The reaction vessel was purged with $O_2$ for 5 min before acetaldehyde (224 μL, 4.07 mmol, 10.2 eq.) was added in one portion. The reaction mixture was stirred under 1 atm $O_2$, delivered by inflated balloon, at 23° C. for 5 h. Solvent was removed in vacuo and the residue was dissolved in $CH_2Cl_2$. The organic layer was washed with distilled water and extracted with $CH_2Cl_2$ (3×7 mL). The organic layer was dried over $MgSO_4$ and solvent was removed in vacuo to afford 113 mg of 4-methyl-iodobenzene diacetate (1c) as white solid (84% yield). Characterization of 1c: $^1$H NMR (δ, 23° C., $CDCl_3$): 7.97 (d, J=8.2 Hz, 2H), 7.29 (d, J=8.0 Hz, 2H), 2.44 (s, 3H), 2.00 (s, 6H). $^{13}$C NMR (δ, 23° C., $CDCl_3$): 176.2, 142.5, 134.8, 131.6, 118.2, 21.4, 20.2. The obtained spectral data are in good agreement with those reported in literature. A 20-mL scintillation vial was charged with 4-methyl-iodobenzene diacetate (1c) (100 mg, 0.298 mmol, 1.00 eq.) and 3 M NaOH (5 mL). The reaction mixture was stirred for 3 h at 23° C. The resulting suspension was then filtered to afford 61 mg of 4-methyl iodosylbenzene (2c) as yellow solid (87% yield). Characterization of 2c: $^1$H NMR (δ, 23° C., $CD_3OD$): 7.90 (d, J=8.4 Hz, 2H), 7.38 (d, J=8.2 Hz, 2H), 2.44 (s, 3H). $^{13}$C NMR data have not been collected due to poor solubility of 2c. HRMS (ESI$^+$): Calcd. for $C_7H_8IO$ [M+H]$^+$ m/z 234.9620. Found: 234.9608.

Synthesis of 4-fluoro-iodobenzene diacetate (1d) and 4-fluoro iodosylbenzene (2d)

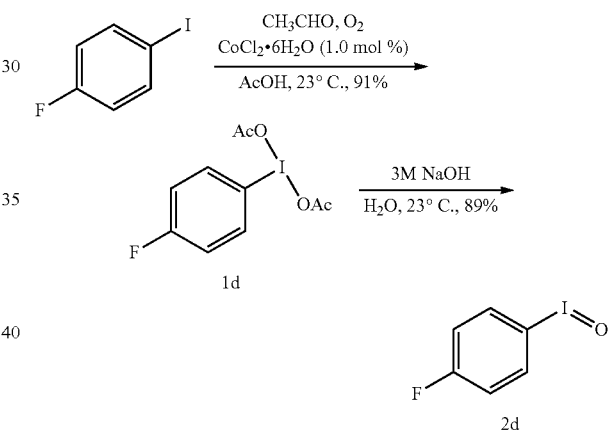

A 20-mL scintillation vial was charged with glacial AcOH (2 mL), 4-fluoro-iodobenzene (89.1 mg, 0.401 mmol, 1.00 eq.) and $CoCl_2 \cdot 6H_2O$ (0.9 mg, 0.004 mmol, 1 mol %) and was fitted with a rubber septum. The reaction vessel was purged with $O_2$ for 5 min before acetaldehyde (224 μL, 4.07 mmol, 10.1 eq.) was added in one portion. The reaction mixture was stirred under 1 atm $O_2$, delivered by inflated balloon, at 23° C. for 5 h. Solvent was removed in vacuo and the residue was dissolved in $CH_2Cl_2$. The organic layer was washed with distilled water and extracted with $CH_2Cl_2$ (3×7 mL). The organic layer was dried over $MgSO_4$ and solvent was removed in vacuo to afford 124 mg of 4-fluoro-iodobenzene diacetate (1d) as white solid (91% yield). Characterization of 1d: $^1$H NMR (δ, 23° C., $CDCl_3$): 8.08 (dd, J=9.1, 4.9 Hz, 2H), 7.18 (t, J=8.6 Hz, 2H), 2.01 (s, 6H). $^{13}$C NMR (δ, 23° C., $CDCl_3$): 176.3, 164.2 (d, J=253.1 Hz), 137.4 (d, J=8.7 Hz), 118.4 (d, J=22.6 Hz), 115.4, 20.2. The obtained spectral data are in good agreement with those reported in literature.

A 20-mL scintillation vial was charged with 4-fluoro-iodobenzene diacetate (1d) (101 mg, 0.298 mmol, 1.00 eq.) and 3 M NaOH (5 mL). The reaction mixture was stirred for 3 h at 23° C. The resulting suspension was then filtered to afford 63 mg of 4-fluoro-iodosylbenzene (2d) as yellow solid (89% yield). Characterization of 2d: $^1$H NMR ($\delta$, 23° C., CD$_3$OD): 8.06 (dd, J=7.8, 5.4 Hz, 2H), 7.33 (t, J=8.7 Hz, 2H). $^{13}$C NMR data have not been collected due to poor solubility of 2d. HRMS (ESI$^+$): Calcd. for C$_6$H$_5$FIO [M+H]$^+$ m/z 238.9369. Found: 238.9357.

Synthesis of 3-bromo-iodobenzene diacetate (1e) and 3-bromo iodosylbenzene (2e)

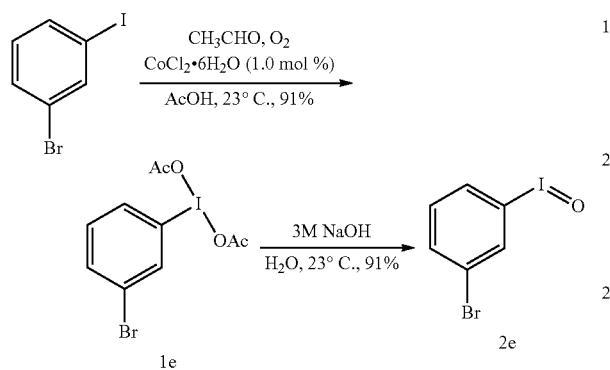

A 20-mL scintillation vial was charged with glacial AcOH (2 mL), 3-bromo-iodobenzene (113 mg, 0.399 mmol, 1.00 eq.) and CoCl$_2$.6H$_2$O (0.9 mg, 0.004 mmol, 1 mol %) and was fitted with a rubber septum. The reaction vessel was purged with O$_2$ for 5 min before acetaldehyde (224 µL, 4.07 mmol, 10.2 eq.) was added in one portion. The reaction mixture was stirred under 1 atm O$_2$, delivered by inflated balloon, at 23° C. for 5 h. Solvent was removed in vacuo and the residue was dissolved in CH$_2$Cl$_2$. The organic layer was washed with distilled water and extracted with CH$_2$Cl$_2$ (3×7 mL). The organic layer was dried over MgSO$_4$ and solvent was removed in vacuo to afford 146 mg of 3-bromo-iodobenzene diacetate (1e) as white solid (91% yield). Characterization of 1e: $^1$H NMR ($\delta$, 23° C., CDCl$_3$): 8.22 (s, 1H), 8.02 (d, J=8.1 Hz, 1H), 7.71 (d, J=8.1 Hz, 1H), 7.37 (d, J=8.0 Hz, 1H), 2.02 (s, 6H). $^{13}$C NMR ($\delta$, 23° C., CDCl$_3$): 176.8, 137.5, 135.1, 133.6, 132.3, 124.1, 121.5, 20.6. The obtained spectral data are in good agreement with those reported in literature.

A 20-mL scintillation vial was charged with 3-bromo-iodobenzene diacetate (1e) (121 mg, 0.302 mmol, 1.00 eq.) and 3 M NaOH (5 mL). The reaction mixture was stirred for 3 h at 23° C. The resulting suspension was then filtered to afford 82 mg of 3-bromo-iodosylbenzene (2e) as yellow solid (91% yield). Characterization of 2e: $^1$H NMR ($\delta$, 23° C., CD$_3$OD): 8.18 (s, 1H), 8.00 (d, J=8.0 Hz, 1H), 7.75 (d, J=8.0 Hz, 1H), 7.53-7.47 (m, 1H). $^{13}$C NMR data have not been collected due to poor solubility of 2e. HRMS (ESI$^+$): Calcd. for C$_6$H$_5$BrIO [M+H]$^+$ m/z 298.8568. Found: 298.8556.

Synthesis of µ-oxa-bis[(acetoxyiodo)-4-trifluoromethyl-benzene] (1f) and 4-trifluoromethyl iodosylbenzene (2f)

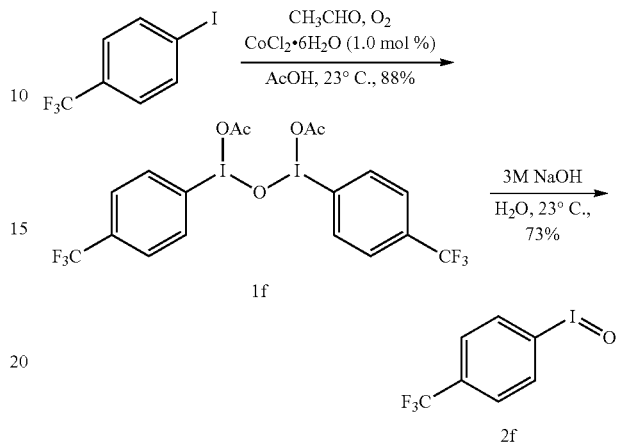

A 20-mL scintillation vial was charged with glacial AcOH (2 mL), 4-trifluoromethyl-iodobenzene (109 mg, 0.402 mmol, 1.00 eq.) and CoCl$_2$.6H$_2$O (0.9 mg, 0.004 mmol, 1 mol %) and was fitted with a rubber septum. The reaction vessel was purged with O$_2$ for 5 min before acetaldehyde (224 µL, 4.07 mmol, 10.1 eq.) was added in one portion. The reaction mixture was stirred under 1 atm O$_2$, delivered by inflated balloon, at 23° C. for 5 h. The solvent was removed in vacuo and residue was dissolved in CH$_2$Cl$_2$. The organic layer was washed with distilled water and extracted with CH$_2$Cl$_2$ (3×7 mL). The organic layer was dried over MgSO$_4$ and solvent was removed in vacuo to afford 119 mg of the title compound if as white solid (88% yield). Characterization of 1f: $^1$H NMR ($\delta$, 23° C., CDCl$_3$): 7.92 (d, J=8.3 Hz, 2H), 7.53 (d, J=8.3 Hz, 2H), 1.94 (s, 3H). $^{13}$C NMR of the sample was not recorded as the compound was unstable over the course of the NMR acquisition. The obtained spectral data are in good agreement with those reported in literature.

A 20-mL scintillation vial was charged with µ-oxa-bis[(acetoxyiodo)-4-trifluoromethyl-benzene] (1f) (78.3 mg, 0.115 mmol, 1.00 eq.) and 3 M NaOH (5 mL). The reaction mixture was stirred for 3 h at 23° C. The resulting suspension was then filtered to afford 48 mg of 4-trifluoromethyl iodosylbenzene (2f) as yellow solid (73% yield). Characterization of 2f: $^1$H NMR ($\delta$, 23° C., CD$_3$OD): 8.23 (d, J=8.3 Hz, 2H), 7.90 (d, J=8.3 Hz, 2H). $^{13}$C NMR data have not been collected due to poor solubility of 2b. HRMS (ESI$^+$): Calcd. for C$_7$H$_5$F$_3$IO [M+H]$^+$ m/z 288.9337. Found: 288.9324.

Synthesis of 3,5-dimethyl-iodobenzene diacetate (1g) and 3,5-dimethyl iodosylbenzene (2g)

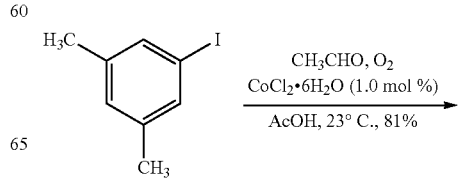

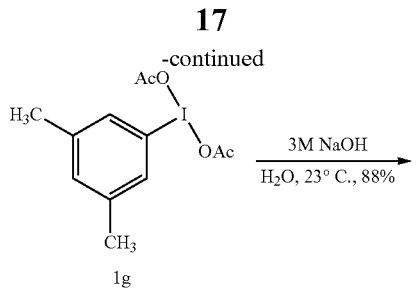

A 20-mL scintillation vial was charged with glacial AcOH (2 mL), 3,5-dimethyl-iodobenzene (93.1 mg, 0.401 mmol, 1.00 eq.) and $CoCl_2 \cdot 6H_2O$ (0.9 mg, 0.004 mmol, 1 mol %) and was fitted with a rubber septum. The reaction vessel was purged with $O_2$ for 5 min before acetaldehyde (224 μL, 4.07 mmol, 10.1 eq.) was added in one portion. The reaction mixture was stirred under 1 atm $O_2$, delivered by inflated balloon, at 23° C. for 10 h. Solvent was removed in vacuo and the residue was dissolved in $CH_2Cl_2$. The organic layer was washed with distilled water and extracted with $CH_2Cl_2$ (3×7 mL). The organic layer was dried over $MgSO_4$ and solvent was removed in vacuo to afford 114 mg of 3,5-dimethyl-iodobenzene diacetate (1g) as white solid (81% yield). Characterization of 1g: $^1$H NMR (δ, 23° C., $CDCl_3$): 7.72 (s, 2H), 7.20 (s, 1H), 2.38 (s, 6H), 2.00 (s, 6H). $^{13}$C NMR (δ, 23° C., $CDCl_3$): 176.4, 141.1, 133.7, 132.5, 121.3, 21.3, 20.4. The obtained spectral data are in good agreement with those reported in literature.

A 20-mL scintillation vial was charged with 3,5-dimethyl-iodobenzene diacetate (1g) (106 mg, 0.303 mmol) and 3 M NaOH (5 mL). The reaction mixture was stirred for 3 h at 23° C. The resulting suspension was then filtered to afford 66 mg of 3,5-dimethyl-iodosylbenzene (2g) as yellow solid (88% yield). Characterization of 2g: $^1$H NMR (δ, 23° C., $CD_3OD$): 7.66 (s, 2H), 7.24 (s, 1H), 2.39 (s, 6H). $^{13}$C NMR data have not been collected due to poor solubility of 2g. HRMS (ESI$^+$): Calcd. for $C_8H_{10}IO$ [M+H]$^+$ m/z 248.9776. Found: 248.9763.

Synthesis of hydroxy(phenyl)-λ3-iodaneyl 4-methylbenzenesulfonate (3)

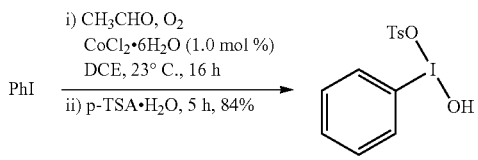 [SMILES: "PhI" ; Cc1ccc(S(=O)(=O)OI(O)c2ccccc2)cc1]

A 20-mL scintillation vial was charged with DCE (2 mL), iodobenzene (88 mg, 0.431 mmol, 1.00 eq.) and $CoCl_2 \cdot 6H_2O$ (0.9 mg, 0.004 mmol, 1 mol %) and was fitted with a rubber septum. The reaction vessel was purged with $O_2$ for 5 min before acetaldehyde (224 μL, 4.06 mmol, 10.2 eq.) was added in one portion. The reaction mixture was stirred under 1 atm $O_2$, delivered by inflated balloon, at 23° C., for 16 h. Then p-TSA.H$_2$O (90 mg, 0.475 mmol, 1.10 eq.) dissolved in minimum amount of acetonitrile at room temperature and added to the reaction mixture via syringe. It was then stirred for 5 h, white solid residue was filtered, washed with little acetonitrile in hexane, dried in vacuo to afford 141 mg of the title compound as white solid (84% yield). $^1$H NMR (δ, 23° C., MeOD): 8.36 (d, J=8.2 Hz, 2H), 7.87-7.82 (m, 1H), 7.73-7.66 (m, 4H), 7.23 (d, J=8.1 Hz, 2H), 2.37 (s, 3H). $^{13}$C NMR (δ, 23° C., MeOD): 143.0, 141.9, 137.0, 134.9, 132.8, 129.8, 126.9, 122.1, 21.3.

Synthesis of 1,3-Dihydro-1-hydroxy-3,3-dimethyl-1, 2-benziodoxole (5)

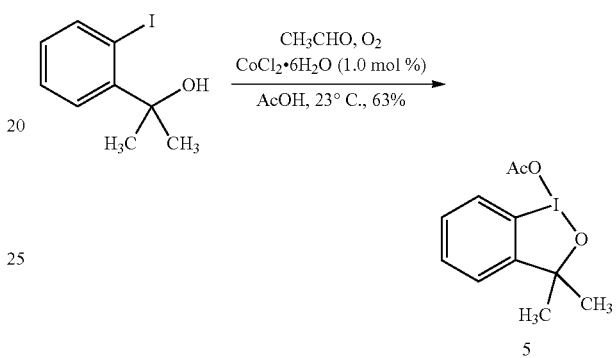

A 20-mL scintillation vial was charged with glacial AcOH (2 mL), 2-(2-iodophenyl)propan-2-ol (75.9 mg, 0.290 mmol, 1.00 eq.) and $CoCl_2 \cdot 6H_2O$ (0.7 mg, 0.003 mmol, 1 mol %) and was fitted with a rubber septum. The reaction vessel was purged with $O_2$ for 5 min before acetaldehyde (168 μL, 2.99 mmol, 10.3 eq.) was added in one portion. The reaction mixture was stirred under 1 atm $O_2$, delivered by inflated balloon, at 23° C. for 10 h. The solvent was removed in vacuo and residue was dissolved in $CH_2Cl_2$. The organic layer was washed with distilled water and extracted with $CH_2Cl_2$ (3×7 mL). The organic layer was dried over $MgSO_4$ and solvent was removed in vacuo. The obtained residue was washed with hexanes to afford 59 mg of the title compound as white solid (63% yield). $^1$H NMR (δ, 23° C., $CDCl_3$): 7.79 (d, J=7.5 Hz, 1H), 7.50-7.45 (m, 2H), 7.18 (d, J=9.1 Hz, 1H), 2.11 (s, 3H), 1.52 (s, 6H). $^{13}$C NMR (δ, 23° C., $CDCl_3$): 177.4, 149.4, 130.4, 129.95, 129.87, 126.2, 115.7, 84.6, 29.2, 21.5.

Synthesis of 3,3-bis(trifluoromethyl)-1λ3-benzo[d] [1,2]iodaoxol-1(3H)-yl acetate (6)

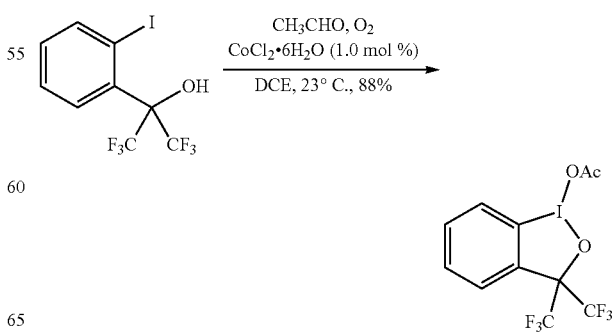

A 20-mL scintillation vial was charged with DCE (2 mL), 1,1,1,3,3,3-hexafluoro-2-(2-iodophenyl)propan-2-ol (149 mg, 0.403 mmol, 1.00 eq.) and CoCl$_2$.6H$_2$O (0.9 mg, 0.004 mmol, 1 mol %) and was fitted with a rubber septum. The reaction vessel was purged with O$_2$ for 5 min before acetaldehyde (224 μL, 4.06 mmol, 10.1 eq.) was added in one portion. The reaction mixture was stirred under 1 atm O$_2$, delivered by inflated balloon, at 23° C., for 16 h. The solvent was removed in vacuo and washed with 5% chloroform in hexane several times. Removal of excess solvent in vacuo afforded 151 mg of the title compound as off white solid (88% yield). $^1$H NMR (δ, 23° C., CDCl$_3$): 7.93 (d, J=8.2 Hz, 1H), 7.61-7.79 (m, 3H), 2.18 (s, 3H). The recorded spectral data are in good agreement with those reported in literature.

Synthesis of 1,3-diacetoxy-1,3-dihydro-1,3,2-benzoiodooxole (7)

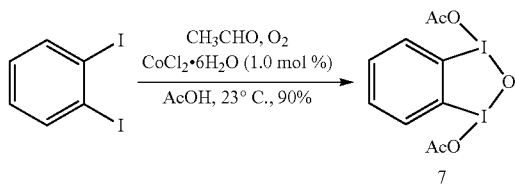 [SMILES: Ic1ccccc1I ; CC(=O)OI1OI(OC(C)=O)c2ccccc21]

A 20-mL scintillation vial was charged with glacial AcOH (2 mL), 1,2-diiodobenzene (132 mg, 0.400 mmol, 1.00 eq.) and CoCl$_2$.6H$_2$O (0.9 mg, 0.004 mmol, 1 mol %) and was fitted with a rubber septum. The reaction vessel was purged with O$_2$ for 5 min before acetaldehyde (224 μL, 4.07 mmol, 10.0 eq.) was added in one portion. The reaction mixture was stirred under 1 atm O$_2$, delivered by inflated balloon, at 23° C. for 10 h. Solvent was reduced in vacuo and hexanes were added. The observed white precipitate was isolated by filtration, washed with hexanes, and dried in vacuo to afford 167 mg of the title compound (90% yield). $^1$H NMR (δ, 23° C., CDCl$_3$): 8.03 (dd, J=6.1, 3.4 Hz, 2H), 7.63 (dd, J=6.1, 3.4 Hz, 2H), 2.09 (s, 6H). $^{13}$C NMR (δ, 23° C., CDCl$_3$): 178.1, 135.3, 131.9, 21.6.

Synthesis of 1-(tert-butylsulfonyl)-2-iodylbenzene (8)

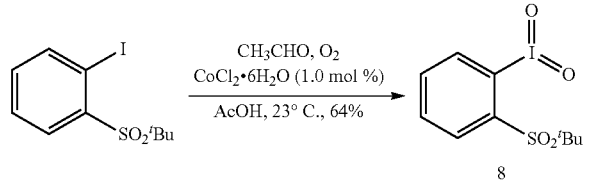

A 20-mL scintillation vial was charged with glacial AcOH (2 mL), 1-(tert-butylsulfonyl)-2-iodobenzene (130 mg, 0.401 mmol, 1.00 eq.) and CoCl$_2$.6H$_2$O (0.9 mg, 0.004 mmol, 1 mol %) and was fitted with a rubber septum. The reaction vessel was purged with O$_2$ for 5 min before acetaldehyde (224 μL, 4.07 mmol, 10.1 eq.) was added in one portion. The reaction mixture was stirred under 1 atm O$_2$, delivered by inflated balloon, at 23° C. for 10 h. The solvent was removed in vacuo and residue was treated with 2:1 hexanes:CH$_2$Cl$_2$ to induce precipitation of white solid. The precipitate was isolated by filtration, washed with hexanes, and dried in vacuo to afford 91 mg of the title compound as white solid (64% yield). Characterization of 8: $^1$H NMR (δ, 23° C., DMSO-d$_6$): 8.46 (d, J=7.6 Hz, 1H), 8.13 (t, J=7.1 Hz, 1H), 7.97-7.84 (m, 2H), 1.32 (s, 9H). $^{13}$C NMR (δ, 23° C., DMSO-d$_6$): 148.0, 135.1, 132.0, 131.2, 124.0, 61.2, 23.2. The spectral data are in good agreement with those reported in literature.

Synthesis of 1-Hydroxy-1,2-benziodoxol-3(1H)-one

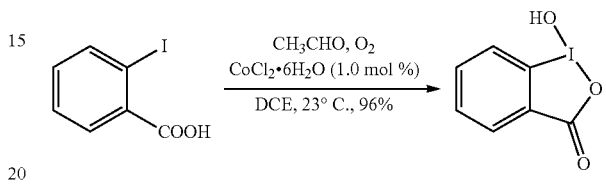

A 20-mL scintillation vial was charged with DCE (2 mL), 2-iodobenzoic acid (50.2 mg, 0.202 mmol, 1.00 equiv) and CoCl2.6H2O (0.5 mg, 0.002 mmol, 1 mol %) and was fitted with a rubber septum. The reaction vessel was purged with O2 for 5 min before acetaldehyde (112 μL, 2.03 mmol, 10.1 equiv) was added in one portion. The reaction mixture was stirred under 1 atm O2, delivered by inflated balloon, at 23° C., for 16 h. The reaction mixture was diluted with hexane and the solid residue was filtered off, washed with 2 mL water. The solid left was dried in vacuo to afford 51 mg of the title compound as off-white solid (96% yield). $^1$H NMR (δ, 23° C., DMSO-d$_6$): 8.03 (s, 1H, OH proton exchangeable with D$_2$O), 8.01-7.98 (m, 1H), 7.95-7.92 (m, 1H), 7.84 (s, 1H), 7.69 (td, J=7.3, 1.0 Hz, 1H). $^{13}$C NMR (δ, 23° C., DMSO-d$_6$): 167.8, 134.5, 131.6, 131.2, 130.4, 126.4, 120.5. mp 247-250° C. (lit. 250-252° C.)

B2. Synthesis of Aryl Hypervalent Iodine (V) Reagents

Synthesis of 1-(tert-butylsulfonyl)-2-iodobenzene (22)

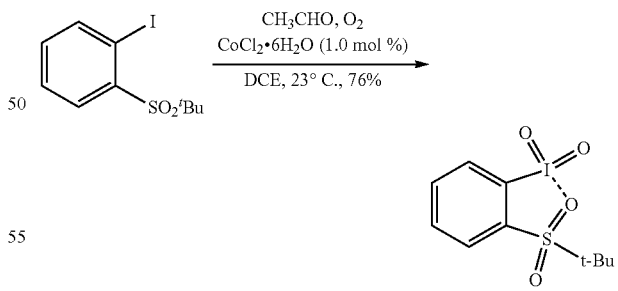

A 20-mL scintillation vial was charged with glacial AcOH (2 mL), 1-(tert-butylsulfonyl)-2-iodobenzene (130 mg, 0.401 mmol, 1.00 equiv) and CoCl$_2$.6H$_2$O (0.9 mg, 0.004 mmol, 1 mol %) and was fitted with a rubber septum. The reaction vessel was purged with O2 for 5 min before acetaldehyde (224 μL, 4.07 mmol, 10.1 equiv) was added in one portion. The reaction mixture was stirred under 1 atm O$_2$, delivered by inflated balloon, at 23° C. for 10 h. The solvent was concentrated to 1 mL under reduced pressure and residue was treated with 2:1 hexanes:CH$_2$Cl$_2$ to induce precipitation of white solid. The precipitate was isolated by filtration, washed with hexanes, and dried in vacuo to afford 108 mg of the title compound as a white solid (76% yield). Characterization of Compound 22: $^1$H NMR (δ, 23° C., DMSO-d$_6$): 8.46 (d, J=7.6 Hz, 1H), 8.13 (t, J=7.1 Hz, 1H), 7.97-7.84 (m, 2H), 1.32 (s, 9H). $^{13}$C NMR (δ, 23° C., DMSO-d$_6$): 148.0, 135.1, 132.0, 131.2, 124.0, 61.2, 23.2. mp 169-170° C. (expl). The spectral data are in good agreement with those reported in literature.

Synthesis of 2-nitroiodylbenzene (24)

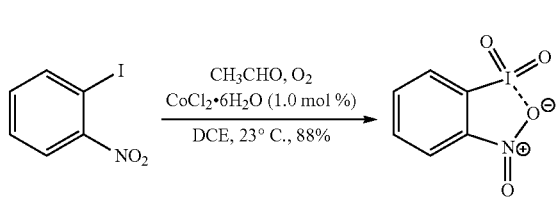

A 20-mL scintillation vial was charged with DCE (2 mL), 2-nitroiodobenzene (51.2 mg, 0.205 mmol, 1.00 equiv) and CoCl$_2$.6H$_2$O (0.5 mg, 0.002 mmol, 1 mol %) and was fitted with a rubber septum. The reaction vessel was purged with O2 for 5 min before acetaldehyde (112 μL, 2.03 mmol, 10.0 equiv) was added in one portion. The reaction mixture was stirred under 1 atm O$_2$, delivered by inflated balloon, at 23° C., for 16 h. The solvent was concentrated to 1 mL under reduced pressure and the resulting solution was diluted with 5 mL hexane to induce precipitation. The precipitate was filtered off to afford 50 mg of the title compound as a pale-yellow solid (88% yield). Characterization of Compound 24: $^1$H NMR (δ, 23° C., DMSO-d$_6$): 8.37 (dd, J=8.1, 1.1 Hz, 1H), 8.30 (dd, J=7.7, 1.3 Hz, 1H), 8.19 (td, J=7.5, 1.0 Hz, 1H), 7.89 (td, J=7.7, 1.1 Hz, 1H). $^{13}$C NMR (δ, 23° C., DMSO-d6): δ 144.5, 144.2, 137.1, 133.4, 125.5, 125.3. mp 196-199° C. HRMS (ESI+): Calcd. for C$_6$H$_4$NINaO$_4$ [M+Na]$^+$ m/z 303.9083. Found: 303.9078.

Synthesis of 2-(2-iodylphenyl)pyridine (25)

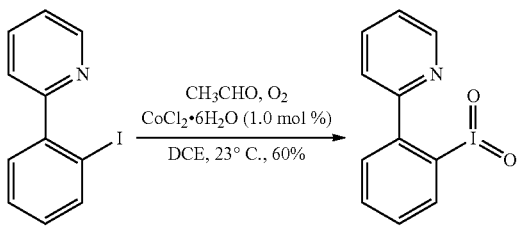 [SMILES: Ic1ccccc1-c1ccccn1 ; O=I(=O)c1ccccc1-c1ccccn1]

A 20-mL scintillation vial was charged with acetic acid (2 mL), 2-(2-iodophenyl)pyridine (79.5 mg, 0.283 mmol, 1.00 equiv) and CoCl$_2$.6H$_2$O (0.7 mg, 0.003 mmol, 1 mol %) and was fitted with a rubber septum. The reaction vessel was purged with O$_2$ for 5 min before acetaldehyde (149 μL, 2.71 mmol, 10.0 equiv) was added in one portion. The reaction mixture was stirred under 1 atm O$_2$, delivered by inflated balloon, at 23° C., for 16 h. The solvent was concentrated to 1 mL under reduced pressure and residue was treated with 2:1 hexanes: CHCl$_3$ to induce precipitation. The precipitate was then filtered off and washed with hexane to afford 53 mg of the title compound as off-white solid (60% yield). Characterization of Compound 25: $^1$H NMR (δ, 23° C., D20): 8.69 (dd, J=5.1, 0.8 Hz, 1H), 8.37-8.30 (m, 2H), 8.24 (d, J=8.2 Hz, 1H), 8.13 (td, J=7.8, 1.4 Hz, 1H), 7.87 (td, J=7.6, 1.7 Hz, 2H), 7.59 (ddd, J=7.5, 5.2, 1.1 Hz, 1H). $^{13}$C NMR (δ, 23° C., D20): 149.3, 144.8, 142.3, 140.9, 134.1, 132.6, 132.0, 127.3, 125.4, 124.0, 120.5. mp 170-172° C. (decomp). HRMS (ESI+): Calcd for C$_{11}$H$_8$INNaO$_2$ [M+Na]$^+$ m/z 335.9497. Found: 335.9487.

Synthesis of p-methyliodylbenzene (29)

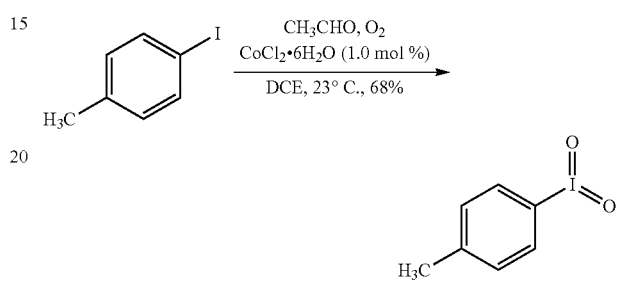

A 20-mL scintillation vial was charged with DCE (2 mL), 4-iodotoluene (87.1 mg, 0.399 mmol, 1.00 equiv) and CoCl$_2$.6H$_2$O (0.9 mg, 0.004 mmol, 1 mol %) and was fitted with a rubber septum. The reaction vessel was purged with O$_2$ for 5 min before acetaldehyde (224 μL, 4.07 mmol, 10.0 equiv) was added in one portion. The reaction mixture was stirred under 1 atm O2, delivered by inflated balloon, at 23° C., for 16 h. The solvent was concentrated to 1 mL under reduced pressure and the resulting solution was diluted with 5 mL hexane. The precipitate was filtered off to afford 67 mg of the title compound as a yellow-white powder (68% yield). Characterization of Compound 29: $^1$H NMR (δ, 23° C., DMSO-d$_6$): 7.83 (d, J=8.2 Hz, 2H), 7.39 (d, J=7.9 Hz, 2H), 2.38 (s, 3H). $^{13}$C NMR (δ, 23° C., DMSO-d$_6$): 141.4, 136.9, 131.5, 129.4, 126.5, 20.9. HRMS (ESI+): Calcd for C$_7$H$_7$INaO$_2$ [M+Na]$^+$ m/z 272.9388. Found: 272.9387. mp 190-192° C. (decomp) lit. 213° C. (decomp). The spectral data are in good agreement with those reported in literature.

Synthesis of p-fluoroiodylbenzene (30)

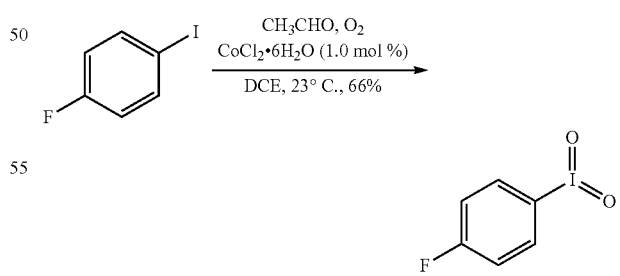

A 20-mL scintillation vial was charged with DCE (2 mL), 4-fluoroiodobenzene (89.3 mg, 0.401 mmol, 1.00 equiv) and CoCl$_2$.6H$_2$O (0.9 mg, 0.004 mmol, 1 mol %) and was fitted with a rubber septum. The reaction vessel was purged with O2 for 5 min before acetaldehyde (224 μL, 4.07 mmol, 10.0 equiv) was added in one portion. The reaction mixture was stirred under 1 atm O$_2$, delivered by inflated balloon, at 23°

C., for 16 h. The solvent was removed in vacuo and the residue was washed with hexanes twice. The residue was dried in vacuo to afford 66 mg of the title compound as a yellow-white powder (66% yield). Characterization of Compound 30: $^1$H NMR ($\delta$, 23° C., DMSO-d$_6$): $\delta$ 8.05-8.00 (m, 2H), 7.46-7.40 (m, 2H). $^{13}$C NMR ($\delta$, 23° C., DMSO-d$_6$): $\delta$ 165.8, 162.5, 129.7 (d, J=36 Hz), 116.2 (d, J=90 Hz). mp 210-212° C. (expl) lit. 234° C. (decomp). HRMS (ESI+): Calcd for C$_6$H$_4$FINaO$_2$ [M+Na]+ m/z 276.9138. Found: 276.9133. The spectral data are in good agreement with those reported in literature.

Synthesis of p-trifluoromethyliodylbenzene (31)

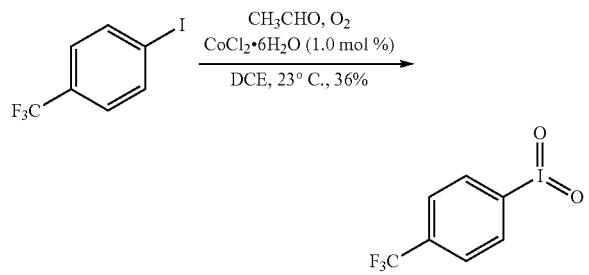

A 20-mL scintillation vial was charged with DCE (2 mL), 4-trifluoromethyliodobenzene (1g, 109 mg, 0.401 mmol, 1.00 eq.) and CoCl$_2$.6H$_2$O (0.9 mg, 0.004 mmol, 1 mol %) and was fitted with a rubber septum. The reaction vessel was purged with O2 for 5 min before acetaldehyde (224 μL, 4.07 mmol, 10.0 eq.) was added in one portion. The reaction mixture was stirred under 1 atm O$_2$, delivered by inflated balloon, at 23° C., for 16 h. The solvent was removed in vacuo and the residue was washed with hexanes twice. The residue was dried in vacuo to afford 43 mg of the title compound as a yellow-white powder (36% yield). Characterization of Compound 31: $^1$H NMR ($\delta$, 23° C., DMSO-d$_6$): 8.17 (d, J=7.6 Hz, 2H), 7.95 (d, J=8.0 Hz, 2H). HRMS (ESI+): Calcd for C$_7$H$_4$F$_3$INaO$_2$ [M+Na]$^+$ m/z 326.9106. Found: 326.9102. mp 232-234° C. (decomp) lit. 213-216° C. (decomp). The spectral data are in good agreement with those reported in literature.

Synthesis of 3,5-dimethyliodylbenzene (26)

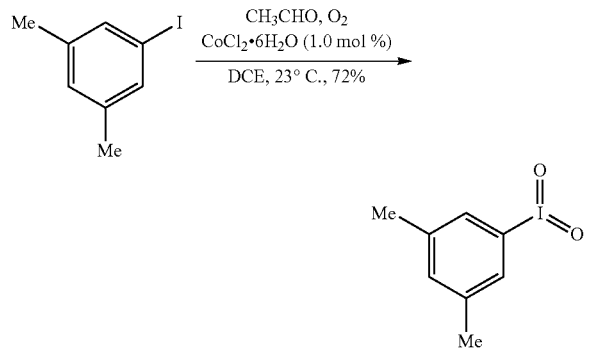

A 20-mL scintillation vial was charged with DCE (2 mL), 3,5-dimethyliodobenzene (93.2 mg, 0.401 mmol, 1.00 equiv) and CoCl$_2$.6H$_2$O (0.9 mg, 0.004 mmol, 1 mol %) and was fitted with a rubber septum. The reaction vessel was purged with O2 for 5 min before acetaldehyde (224 μL, 4.07 mmol, 10.1 equiv) was added in one portion. The reaction mixture was stirred under 1 atm O$_2$, delivered by inflated balloon, at 23° C., for 16 h. The solvent was removed in vacuo and the residue was washed with hexane twice. The residue was dried in vacuo to afford 76 mg of the title compound as off-white solid (72% yield). Characterization of Compound 26: $^1$H NMR ($\delta$, 23° C., DMSO-d$_6$): 7.55 (s, 2H), 7.19 (s, 1H), 2.35 (s, 6H). mp 196-198° C. (decomp) lit. 217° C. (expl). The spectral data are in good agreement with those reported in literature.

Synthesis of 3-bromoiodylbenzene (27)

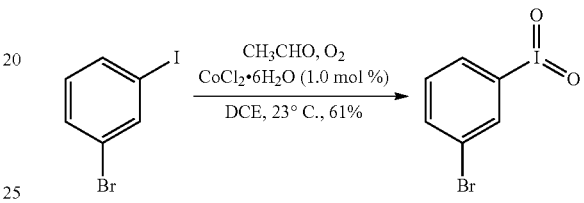

A 20-mL scintillation vial was charged with DCE (2 mL), 3-bromoiodobenzene (113 mg, 0.399 mmol, 1.00 equiv) and CoCl$_2$.6H$_2$O (0.9 mg, 0.004 mmol, 1 mol %) and was fitted with a rubber septum. The reaction vessel was purged with O2 for 5 min before acetaldehyde (224 μL, 4.07 mmol, 10.2 equiv) was added in one portion. The reaction mixture was stirred under 1 atm O2, delivered by inflated balloon, at 23° C., for 16 h. The solvent was removed in vacuo and the residue was washed with hexane twice. The residue was dried in vacuo to afford 77 mg of the title compound as an off-white powder (61% yield). Characterization of Compound 27: $^1$H NMR ($\delta$, 23° C., DMSOd$_6$): 8.08 (s, 1H), 7.95 (d, J=7.9 Hz, 1H), 7.74 (dt, J=7.9, 0.9 Hz, 1H), 7.54 (t, J=7.8 Hz, 1H). $^{13}$C NMR ($\delta$, 23° C., DMSO-d$_6$): 153.2, 133.9, 131.1, 128.9, 125.5, 121.7. mp 204-206° C. (decomp). HRMS (ESI+): Calcd for C$_6$H$_4$IBrNaO$_2$ [M+Na]$^+$ m/z 336.8337. Found: 336.8332.

C. Application of Aerobic Oxidation to Organic Oxidation Chemistry

C1. ArI-Catalyzed Aerobic Oxidation of Secondary Alcohols

This example demonstrates that catalytic amounts of aryl iodides can be used to oxidize organic compounds, e.g., alcohols to aldehydes, in the presence of an aliphatic aldehyde and dioxygen.

Method A:

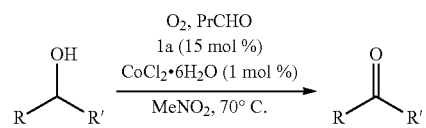

A 25-mL three-neck flask fitted with condenser (5° C.) was charged with nitromethane (5 mL), 1-(tert-butylsulfonyl)-2-iodobenzene (32.4 mg, 0.100 mmol, 15.0 mol %) and CoCl$_2$.6H$_2$O (1.70 mg, 0.007 mmol, 1.04 mol %). O2 was bubbled through the reaction before butyraldehyde (90 µL, 1.0 mmol, 1.5 equiv) was added in one portion and stirred at 23° C. for 20 min. Then subsequent alcohol (4, 0.667 mmol, 1.0 equiv) was dissolved in 1.0 ml nitromethane (CH₂Cl₂ was used where the alcohol was insoluble in nitromethane) and delivered via syringe to the reaction mixture. The reaction mixture was stirred under constant O₂ bubbling (at the approximate flow rate of 30-35 mL/min), at 70° C. Three more portions of butyraldehyde (90.0 µL, 1.00 mmol, 1.49 equiv) was added at an interval of 2 h and the reaction was stirred for 14 h in total. Then the solvent was reduced and reaction mixture was diluted with dichloromethane, washed with water followed by satd. NaHCO₃ solution and dried over anhyd. MgSO₄. The solvent was concentrated under reduced pressure, purified by column chromatography to afford corresponding ketone.

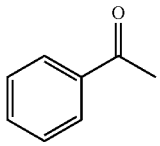

Acetophenone (5b). Purified by silica-gel column chromatography (10% Ethyl acetate in Hexanes). Yield: 64 mg (80%). ¹H NMR (δ, 23° C., CDCl₃): 7.96 (dd, J=8.4, 1.3 Hz, 2H), 7.59-7.53 (m, 1H), 7.44-7.49 (m, 2H), 2.61 (s, 3H). The spectral data are in good agreement with those reported in literature.

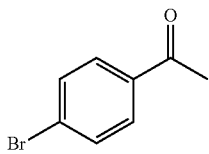

4-Bromoacetophenone (5c). Purified by silica-gel column chromatography (10% Ethyl acetate in Hexanes). Yield: 121 mg (91%). 1H NMR (δ, 23° C., CDCl3): 7.82 (d, J=7.4 Hz, 2H), 7.60 (d, J=7.2 Hz, 2H), 2.58 (s, 3H). mp 50-53° C. (lit. 49-51° C.). The spectral data are in good agreement with those reported in literature.

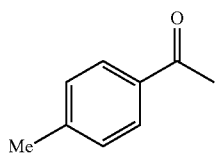

4-Methylacetophenone (5d). Purified by silica-gel column chromatography (10% Ethyl acetate in Hexanes). Yield: 71 mg (79%). ¹H NMR (δ, 23° C., CDCl₃): 7.86 (d, J=8.1 Hz, 2H), 7.26 (d, J=6.7 Hz, 2H), 2.58 (s, 3H), 2.42 (s, 3H). The spectral data are in good agreement with those reported in literature.

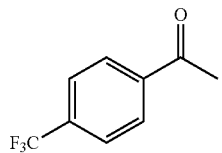

4-Trifluoromethylacetophenone (5e). Purified by silica-gel column chromatography (10% ethyl acetate in hexanes). Yield: 113 mg (90%). ¹H NMR (δ, 23° C., CDCl₃): 8.07 (d, J=8.0 Hz, 2H), 7.74 (d, J=8.0 Hz, 2H), 2.65 (s, 3H). mp 33-35° C. (lit. 30-33° C.). The spectral data are in good agreement with those reported in literature.

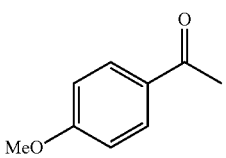

4-Methoxyacetophenone (5f). Purified by silica-gel column chromatography (20% ethyl acetate in hexanes). Yield: 10 mg (9%). ¹H NMR (δ, 23° C., CDCl₃): 7.94 (d, J=8.9 Hz, 2H), 6.93 (d, J=9.0 Hz, 2H), 3.87 (s, 3H), 2.56 (s, 3H). mp 50-53° C. (lit. 49-51° C.). The spectral data are in good agreement with those reported in literature.

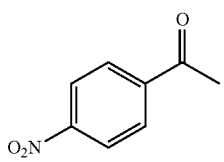

4-Nitroacetophenone (5g). Purified by silica-gel column chromatography (10% ethyl acetate in hexanes). Yield: 95 mg (86%). ¹H NMR (δ, 23° C., CDCl₃): 8.29 (d, J=6.6 Hz, 2H), 8.10 (d, J=6.6 Hz, 2H), 2.66 (s, 3H). mp 77-80° C. (lit. 75-78° C.). The spectral data are in good agreement with those reported in literature.

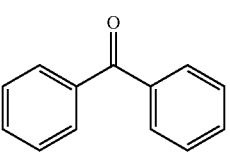 [SMILES: O=C(c1ccccc1)c1ccccc1]

Benzophenone (5h): Purified by silica-gel column chromatography (10% ethyl acetate in hexanes). Yield: 103 mg (85%). ¹H NMR (δ, 23° C., CDCl₃): 7.86 (d, J=7.1 Hz, 4H), 7.67-7.51 (m, 6H). mp 46-48° C. (lit. 47-51° C.). The spectral data are in good agreement with those reported in literature.

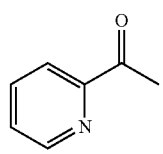

2-Acetylpyridine (5i). Purified by silica-gel column chromatography (25% ethyl acetate in hexanes). Yield: 37 mg (45%). $^1$H NMR (δ, 23° C., CDCl$_3$): 8.68-8.67 m (1H), 8.04-8.02 m (1H), 7.84-7.80 m (1H), 7.48-7.45 m (1H), 2.72 s (3H). The spectral data are in good agreement with those reported in literature.

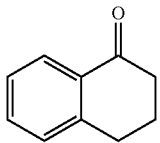

α-Tetralone (5j). Purified by silica-gel column chromatography (10% Ethyl acetate in Hexanes). Yield: 69 mg (73%). $^1$H NMR (δ, 23° C., CDCl$_3$): 8.03 (d, J=7.8 Hz, 1H), 7.46 (td, J=7.5, 1.4 Hz, 1H), 7.32-7.22 (m, 2H), 2.96 (t, J=6.1 Hz, 2H), 2.65 (t, J=6.5 Hz, 2H), 2.14 (t, J=6.4 Hz, 2H). The spectral data are in good agreement with those repoβrted in literature.

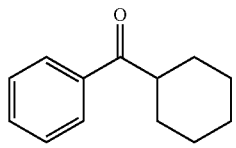 [SMILES: O=C(c1ccccc1)C1CCCCC1]

Phenylcyclohexyl ketone (5k). Purified by silica-gel column chromatography (10% ethyl acetate in hexanes). Yield: 79 mg (64%). $^1$H NMR (δ, 23° C., CDCl$_3$): 7.97 (d, J=8.1 Hz, 2H), 7.56 (t, J=7.2 Hz, 1H), 7.48 (t, J=7.6 Hz, 2H), 3.33-3.24 (m, 1H), 1.94-1.86 (m, 4H), 1.79-1.74 (m, 1H), 1.59-1.27 (m, 5H). mp 56-58° C. (lit. 55-57° C.). The spectral data are in good agreement with those reported in literature.

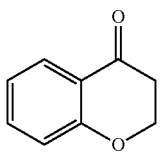 [SMILES: O=C1CCOc2ccccc21]

4-Chromanone (5l). Purified by silica-gel column chromatography (10% Ethyl acetate in Hexanes). Yield: 59 mg (60%). $^1$H NMR (δ, 23° C., CDCl$_3$): 7.89 (dd, J=8.1, 1.5 Hz, 1H), 7.50-7.42 (m, 1H), 7.04-6.94 (m, 2H), 4.53 (t, J=6.6 Hz, 2H), 2.80 (t, J=6.6 Hz, 2H). mp 37-40° C. (lit. 35-38° C.). The spectral data are in good agreement with those reported in literature.

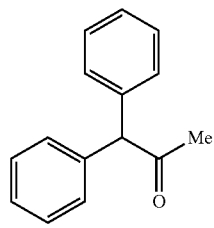 [SMILES: CC(=O)C(c1ccccc1)c1ccccc1]

Diphenylacetone (5p). Purified by silica-gel column chromatography (10% Ethyl acetate in Hexanes). Yield: 46 mg (33%). $^1$H NMR (δ, 23° C., CDCl$_3$): 7.33-7.18 (m, 10H), 5.08 (s, 1H), 2.21 (s, 3H). mp 60-62° C. (lit. 59-63° C.). The spectral data are in good agreement with those reported in literature.

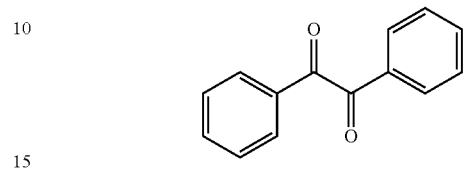

Benzil (5q). Purified by silica-gel column chromatography (10% ethyl acetate in hexanes). Yield: 97 mg (69%). $^1$H NMR (δ, 23° C., CDCl$_3$): 7.98 (d, J=7.0 Hz, 4H), 7.66 (t, J=7.4 Hz, 2H), 7.52 (t, J=7.8 Hz, 4H). mp 91-93° C. (lit. 94-95° C.). The spectral data are in good agreement with those reported in literature.

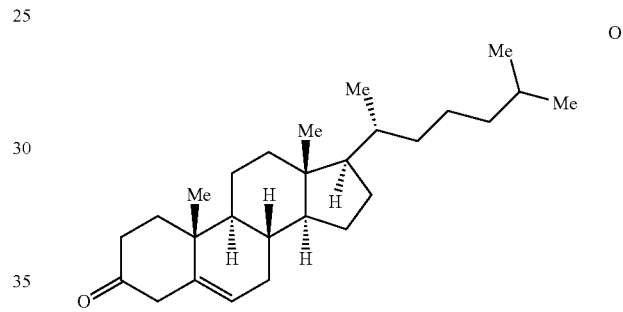

Cholest-5-ene-3-one (5s). Purified by silica-gel column chromatography (10% ethyl acetate in hexanes). Yield: 146 mg (57%). mp 126-128° C. (lit. 129° C.).

Method B:

A 25-mL Schlenck tube was charged with nitromethane (1 mL), 1-(tert-butylsulfonyl)-2-iodobenzene (1a, 32.4 mg, 0.100 mmol, 15.0 mol %) and CoCl$_2$.6H$_2$O (1.70 mg, 0.007 mmol, 1.04 mol %). O$_2$ was bubbled through the reaction before butyraldehyde (250 µL, 2.78 mmol, 4.14 equiv) was added in one portion and stirred at room temperature for 20 min. Then subsequent alcohol (4, 0.670 mmol, 1.00 equiv) was dissolved in 1.0 ml nitromethane and delivered via syringe to the reaction mixture. The reaction mixture was stirred under O$_2$ atmosphere at 70° C. for 12 h. Then the crude reaction mixture was analyzed by GC.

Cyclohexanone (5a). Yield: 86% (b.p.=155° C.), crude reaction mixture was measured from GC with mesitylene as internal standard.

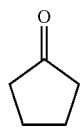

Cyclopentanone (5m). Yield: 77% (b.p.=130.6° C.), crude reaction mixture was measured in GC with mesitylene (b.p.=164.7° C.) as internal standard.

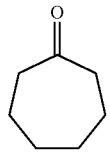

Cycloheptanone (5n). Yield: 91% (b.p.=181.0° C.), crude reaction mixture was measured in GC with mesitylene (b.p.=164.7° C.) as internal standard.

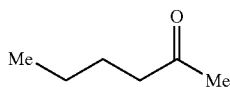

Hexanone (5o). Yield: 71% (b.p.=127° C.), crude reaction mixture was measured in GC with mesitylene (b.p.=164.7° C.) as internal standard.

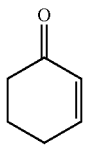

Cyclohex-2-ene-1-one (5r). Yield: 40% (b.p.=173.0° C.), crude reaction mixture was measured in GC with mesitylene (b.p.=164.7° C.) as internal standard.

Catalytic Oxidation of Cyclohexanol in Presence of Air

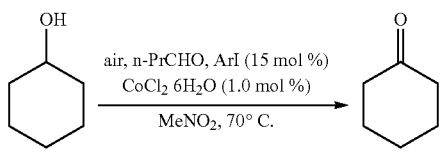

A 25-mL Schlenck tube was charged with nitromethane (1 mL), 1-(tert-butylsulfonyl)-2-iodobenzene (32.4 mg, 0.100 mmol, 15.0 mol %) and $CoCl_2 \cdot 6H_2O$ (1.70 mg, 0.007 mmol, 1.04 mol %). Air was bubbled through the reaction before butyraldehyde (250 μL, 2.78 mmol, 4.14 equiv) was added in one portion and stirred at room temperature for 20 min. Then cyclohexanol (67.1 mg, 0.671 mmol, 1.00 equiv) was dissolved in 1.0 ml nitromethane and delivered via syringe to the reaction mixture. The reaction mixture was stirred under air (with flow rate of 30-35 mL/min) at 70° C. for 12 h. Then the crude reaction mixture was analyzed by GC with the yield determined to be 66%

ArI-Catalyzed Aerobic Oxidation of Primary Alcohols

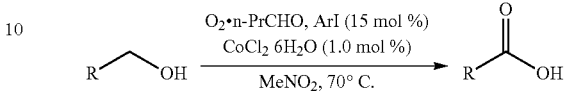

Method A:

A 25-mL three-neck flask fitted with condenser (5° C.) was charged with nitromethane (5 mL), 1-(tert-butylsulfonyl)-2-iodobenzene (1a, 32.4 mg, 0.100 mmol, 15.0 mol %) and $CoCl_2 \cdot 6H_2O$ (1.70 mg, 0.007 mmol, 1.04 mol %). O2 was bubbled through the reaction before butyraldehyde (90 μL, 1.0 mmol, 1.5 equiv) was added in one protion and stirred at room temperature for 20 min. Then, alcohol (6, 0.667 mmol, 1.00 equiv) was dissolved in 1.0 ml nitromethane ($CH_2Cl_2$ was used where the alcohol was insoluble in nitromethane) and delivered via syringe to the reaction mixture. The reaction mixture was stirred under constant O2 bubbling (at the approximate flow rate of 30-35 mL/min), at 70° C. Three more portions of butyraldehyde (90.0 μL, 1.00 mmol, 1.49 equiv) was added at an interval of 2 h and the reaction was stirred for 14 h in total. Then the solvent was reduced and crude reaction mixture was analyzed.

Benzoic acid (7a). Purified by silica-gel column chromatography (10% Ethyl acetate in Hexanes). Yield: 66 mg (81%). $^1$H NMR (δ, 23° C., $CDCl_3$): 8.12 (d, J=7.0 Hz, 2H), 7.65-7.60 (m, 1H), 7.48 (t, J=7.5 Hz, 2H). mp 124-126° C. (lit. 121-125° C.).

3-Chlorobenzoic acid (7c). Purified by silica-gel column chromatography (10% Ethyl acetate in Hexanes). Yield: 90 mg (86%). $^1$H NMR (δ, 23° C., $CDCl_3$): 8.10 (t, J=1.8 Hz, 1H), 8.02 (t, J=1.3 Hz, 1H), 7.60 (ddd, J=8.0, 2.1, 1.1 Hz, 1H), 7.43 (t, J=7.9 Hz, 1H). mp 150-153° C. (lit. 153-157° C.).

4-Picolinic acid or Isonicotinic acid (7d). The general procedure for Method B was modified for this substrate in that the reaction was carried out on a 0.34 mmol scale. Purified by silica-gel column chromatography (5% MeOH in $CH_2Cl_2$). Yield: 26 mg (61%). 1H NMR (δ, 23° C., DMSO-d6): 8.78 (d, J=6.0 Hz, 2H), 7.82 (d, J=6.0 Hz, 2H). mp>300° C. (lit.>300° C.). The spectral data are in good agreement with those reported in literature.

Method B:

A 25-mL Schlenck tube was charged with nitromethane (1 mL), 1-(tert-butylsulfonyl)-2-iodobenzene (1a, 32.4 mg, 0.100 mmol, 15.0 mol %) and $CoCl_2 \cdot 6H_2O$ (1.70 mg, 0.007 mmol, 1.04 mol %). $O_2$ was bubbled through the reaction before butyraldehyde (250 μL, 2.78 mmol, 4.14 equiv) was added in one portion and stirred at room temperature for 20 min. Then subsequent alcohol (6, 0.667 mmol, 1.00 equiv) was dissolved in 1.0 ml nitromethane and delivered via syringe to the reaction mixture. The reaction mixture was stirred under $O_2$ atmosphere at 70° C. for 12 h. Then the crude reaction mixture was analyzed by GC.

Heptanoic acid (7e). Yield: 59% (b.p.=223.0° C.), crude reaction mixture was measured in GC with mesitylene (b.p.=164.7° C.) as internal standard.

Nonanoic acid (70. Yield: 63% (b.p.=269.0° C.), crude reaction mixture was measured in GC with mesitylene (b.p.=164.7° C.) as internal standard.

ArI-Catalyzed Aerobic Oxidation of Diols
Oxidation of Hydroxybenzoin (8)

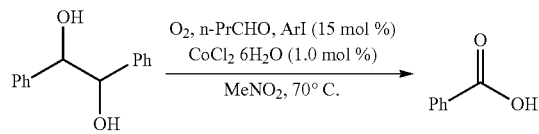 [SMILES: OC(c1ccccc1)C(O)c1ccccc1 ; O=C(O)c1ccccc1]

A 25-mL three-neck flask fitted with condenser (5° C.) was charged with nitromethane (5 mL), hydroxybenzoin (8, 143 mg, 0.67 mmol, 1.0 equiv), 1-(tert-butylsulfonyl)-2-iodobenzene (1a, 32 mg, 0.10 mmol, 15 mol %) and $CoCl_2 \cdot 6H_2O$ (1.70 mg, 0.007 mmol, 1.04 mol %). $O_2$ was bubbled through the reaction before butyraldehyde (90 μL, 1.0 mmol, 1.5 equiv) was added in one portion and stirred at room temperature for 20 min. The reaction mixture was then heated at 70° C. and stirred under constant $O_2$ bubbling (at the approximate flow rate of 30-35 mL/min). Three more portions of butyraldehyde (90 μL, 1.0 mmol, 1.5 equiv) were added at an interval of 2 h and the reaction was stirred for 14 h in total. Then crude reaction mixture was concentrated under reduced pressure and purified by silica-gel column chromatography (20% ethyl acetate in hexanes) to afford 130 mg (79%) of the title compound as white solid. $^1$H NMR (δ, 23° C., $CDCl_3$): 8.12 (d, J=7.0 Hz, 2H), 7.65-7.60 (m, 1H), 7.48 (t, J=7.5 Hz, 2H). mp 126-129° C. (lit. 121-125° C.). The spectral data are in good agreement with those reported in literature.

Oxidation of benzene-1,2-dimethanol (10)

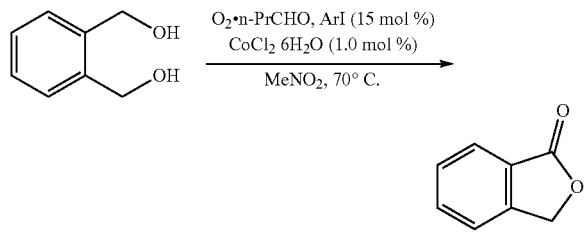

A 25-mL three-neck flask fitted with condenser (5° C.) was charged with nitromethane (5 mL), 1,2-benzenedimethanol (10, 92.5 mg, 0.67 mmol, 1.0 equiv), 1-(tert-butylsulfonyl)-2-iodobenzene (1a, 32 mg, 0.10 mmol, 15 mol %) and $CoCl_2 \cdot 6H_2O$ (1.7 mg, 0.007 mmol, 1.04 mol %). $O_2$ was bubbled through the reaction before butyraldehyde (90 μL, 1.0 mmol, 1.5 equiv) was added in one portion and stirred at 23° C. for 20 min. The reaction mixture was then heated at 70° C. and stirred under constant $O_2$ bubbling (at the approximate flow rate of 30-35 mL/min). Three more portions of butyraldehyde (90 μL, 1.0 mmol, 1.5 equiv) was added at an interval of 2 h and the reaction was stirred for 14 h in total. The crude reaction mixture was concentrated under reduced pressure and purified by silica gel column chromatography (10% ethyl acetate in hexanes) to afford 66 mg (73%) of the title compound as white solid. $^1$H NMR (δ, 23° C., $CDCl_3$): 7.93 (d, J=7.4 Hz, 1H), 7.69 (t, J=7.5 Hz, 1H), 7.56-7.49 (m, 2H), 5.33 (s, 2H). mp 73-75° C. (lit. 75-76° C.). The spectral data are in good agreement with those reported in literature.

C2. Oxidative Dearomatization Chemistry

This example demonstrates oxidation of organic compounds using aryl iodide in the presence of aliphatic aldehyde and dioxygen.

Synthesis of 1-methoxy-1-azaspiro[4.5]deca-6,9-dien-8-one (11)

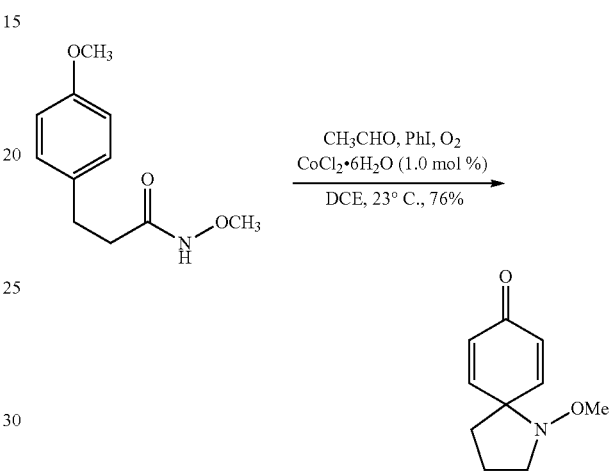

A 20-mL scintillation vial was charged with DCE (2 mL), N-methoxy-3-(4-methoxyphenyl)propanamide (42 mg, 0.201 mmol, 1.0 eq.), iodobenzene (23 μL, 0.201 mmol, 1.00 eq.) and $CoCl_2 \cdot 6H_2O$ (0.5 mg, 0.002 mmol, 1 mol %) and was fitted with a rubber septum. The reaction vessel was purged with $O_2$ for 5 min before acetaldehyde (112 μL, 2.01 mmol, 10.0 eq.) was added in one portion. The reaction mixture was stirred under 1 atm $O_2$, delivered by inflated balloon, at 23° C., for 16 h. The reaction mixture was diluted with DCM, washed with water, 10% $NaHCO_3$ aq. solution, dried over anhydrous $MgSO_4$. The solvent was concentrated under reduced pressure, purified by column chromatography (20%-50% ethyl acetate in hexane) to afford 28 mg of the title compound (76% yield). $^1$H NMR (δ, 23° C., $CDCl_3$): 6.83 (d, J=8.4 Hz, 2H), 6.37 (d, J=8.4 Hz, 2H), 3.79 (s, 3H), 2.54 (t, J=7.9 Hz, 2H), 2.17 (t, J=7.9 Hz, 2H). $^{13}$C NMR (δ, 23° C., $CDCl_3$): 184.5, 171.9, 147.4, 131.3, 65.4, 62.1, 29.8, 27.7, 26.1. The recorded spectral data are in good agreement with those reported in literature.

Synthesis of 2-tosyl-1-phenylethan-1-one (13)

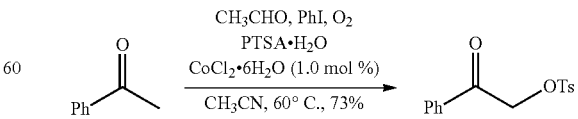

A 50-mL three-neck flask fitted with condenser was charged with acetonitrile (8 mL), acetophenone (62 μL, 0.5 mmol, 1.0 eq.), iodobenzene (67 μL, 0.6 mmol, 1.2 eq.) and $CoCl_2 \cdot 6H_2O$ (1.2 mg, 0.005 mmol, 1 mol %). $O_2$ was bubbled through the reaction before acetaldehyde (168 μL, 3.0 mmol, 15.0 eq.) was added in one portion and stirred at room temperature for 10 min. PTSA.H2O (114 mg, 0.6xx mmol, 1.2xx eq.) was dissolved in 2 ml acetonitrile and delivered via syringe to the reaction mixture. The reaction mixture was stirred under constant $O_2$ bubbling, at 60° C., for 16 h. The reaction mixture was diluted with DCM, washed with water, 10% $NaHCO_3$ aq. solution, dried over $MgSO_4$. The solvent was concentrated under reduced pressure, purified by column chromatography (25% ethyl acetate in hexane) to afford 112 mg of the title compound (73% yield). $^1$H NMR (δ, 23° C., $CDCl_3$): 7.87-7.82 (m, 4H), 7.61 (t, J=7.4 Hz, 1H), 7.47 (t, J=7.5 Hz, 2H), 7.35 (d, J=7.9 Hz, 2H), 5.27 (s, 2H), 2.45 (s, 3H). $^{13}$C NMR (δ, 23° C., $CDCl_3$): 190.4, 145.4, 134.3, 133.9, 132.8, 130.1, 129.1, 128.31, 128.15, 70.1, 21.9. The recorded spectral data are in good agreement with those reported in literature.

Synthesis of
1-oxaspiro[4.5]deca-6,9-diene-2,8-dione (18)

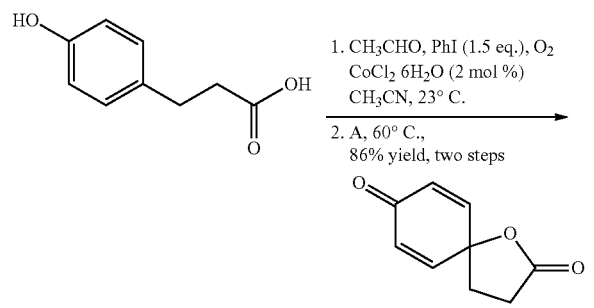

A 20 mL vial was charged with acetonitrile (2 mL), iodobenzene (61.0 mg, 0.299 mmol, 1.50 eq.) and $CoCl_2.6H_2O$ (0.5 mg, 3.85 μmol, 2 mol %) and stoppered with a septum. The reaction vial was purged with $O_2$ for 5 min and then acetaldehyde (168 μL, 3.00 mmol, 15.0 eq.) was added to the reaction mixture. The reaction mixture was stirred for 6 hr at ambient temperature under 1 atm $O_2$ (supplied via a balloon). 3-(4-hydroxyphenyl)propanoic acid (33.2 mg, 0.200 mmol, 1.0 eq.) was added and stirred at 60° C. for 8 h. The solvent was removed in vacuo, diluted with DCM (3 mL), and washed with saturated $NaHCO_3$ aq. solution and water, and dried over anhydrous $MgSO_4$. The solvent was concentrated under reduced pressure and purified by column chromatography on silica gel (50% ethyl acetate in hexane) to afford 28.2 mg of the title compound (86% yield). $^1$H NMR (δ, 23° C., $CDCl_3$): 6.85 (d, J=10.2 Hz, 2H), 6.29 (d, J=10.2 Hz, 2H), 2.79 (t, J=8.3 Hz, 2H), 2.38 (t, J=8.3 Hz, 2H). $^{13}$C NMR (δ, 23° C., $CDCl_3$): 184.07, 175.15, 145.53, 129.16, 78.34, 32.21, 27.93 ppm. The recorded spectral data are in good agreement with those reported in literature.

C3. Alpha-Oxidation of Ketones

Synthesis of 2-tosyl-1-phenylethan-1-one (13)

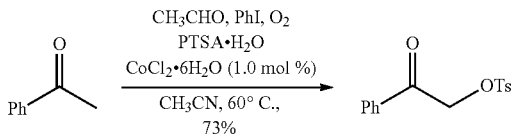

A 50-mL three-neck flask fitted with condenser was charged with acetonitrile (8 mL), acetophenone (62 μL, 0.5xx mmol, 1.0 eq.), iodobenzene (67 μL, 0.6xx mmol, 1.2 eq.) and $CoCl_2.6H_2O$ (1.2 mg, 0.005 mmol, 1 mol %). $O_2$ was bubbled through the reaction before acetaldehyde (168 μL, 3.0 mmol, 15.0 eq.) was added in one portion and stirred at room temperature for 10 min. PTSA.$H_2O$ (114 mg, 0.6 mmol, 1.2 eq.) was dissolved in 2 ml acetonitrile and delivered via syringe to the reaction mixture. The reaction mixture was stirred under constant $O_2$ bubbling, at 60° C., for 16 h. The reaction mixture was diluted with DCM, washed with water, 10% $NaHCO_3$ aq. solution, dried over $MgSO_4$. The solvent was concentrated under reduced pressure, purified by column chromatography (25% ethyl acetate in hexane) to afford 112 mg of the title compound (73% yield). $^1$H NMR (δ, 23° C., $CDCl_3$): 7.87-7.82 (m, 4H), 7.61 (t, J=7.4 Hz, 1H), 7.47 (t, J=7.5 Hz, 2H), 7.35 (d, J=7.9 Hz, 2H), 5.27 (s, 2H), 2.45 (s, 3H). $^{13}$C NMR (δ, 23° C., $CDCl_3$): 190.4, 145.4, 134.3, 133.9, 132.8, 130.1, 129.1, 128.31, 128.15, 70.1, 21.9. The recorded spectral data are in good agreement with those reported in literature.

Synthesis of ethyl
2-methyl-3-oxo-2-(tosyloxy)butanoate (15)

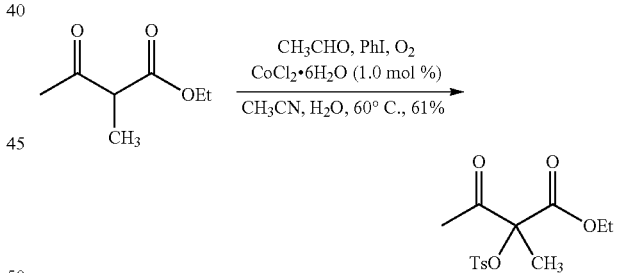

A 50-mL three-neck flask fitted with condenser was charged with acetonitrile (8 mL), 2-methyl ethylacetoacetate (86 mg, 0.597 mmol, 1.00 eq.), iodobenzene (67 μL, 0.602 mmol, 1.01 eq.) and $CoCl_2.6H_2O$ (1.4 mg, 0.006 mmol, 1 mol %). $O_2$ was bubbled through the reaction before acetaldehyde (340 μL, 6.05 mmol, 10.0 eq.) was added in one portion and stirred at room temperature for 10 min. PTSA.$H_2O$ (126 mg, 0.662 mmol, 1.11 eq.) was dissolved in 3 ml acetonitrile and delivered via syringe to the reaction mixture. The reaction mixture was stirred under constant $O_2$ bubbling, at 60° C., for 16 h. The reaction mixture was diluted with DCM, washed with water, 10% $NaHCO_3$ aq. solution, dried over $MgSO_4$. The solvent was concentrated under reduced pressure, purified by column chromatography (25% ethyl acetate in hexane) to afford 114 mg of the title compound (61% yield). $^1$H NMR (δ, 23° C., $CDCl_3$): 7.84

(d, J=8.3 Hz, 2H), 7.34 (d, J=8.0 Hz, 2H), 4.26 (q, J=7.1 Hz, 2H), 2.44 (s, 3H), 2.29 (s, 3H), 1.85 (s, 3H), 1.29 (t, J=7.2 Hz, 3H). $^{13}$C NMR (δ, 23° C., CDCl$_3$): 200.7, 166.6, 145.2, 135.1, 129.9, 127.7, 90.6, 63.0, 25.4, 21.8, 20.2, 13.9. The recorded spectral data are in good agreement with those reported in literature.

Synthesis of ethyl 2-bromo-2-methyl-3-oxobutanoate (16)

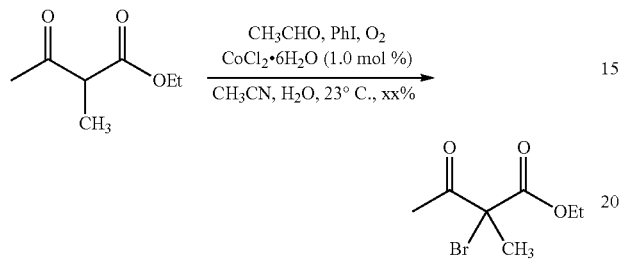

A 20-mL scintillation vial was charged with MeCN:H$_2$O (9:1, 5 mL), 2-methyl ethylacetoacetate (80 mg, 0.554 mmol, 1.00 eq.), iodobenzene (63 μL, 0.564 mmol, 1.02 eq.) and CoCl$_2$.6H$_2$O (1.4 mg, 0.006 mmol, 1 mol %) and was fitted with a rubber septum. The reaction vessel was purged with O$_2$ for 5 min before acetaldehyde (310 μL, 5.52 mmol, 9.96 eq.) was added in one portion. TBABr (200 mg, 0.620 mmol, 1.12 eq.) was dissolved in 2 mL MeCN:H$_2$O (9:1) and added to the reaction mixture via syringe. The reaction mixture was stirred under 1 atm O$_2$, delivered by inflated balloon, at 23° C., for 16 h. The reaction mixture was concentrated under reduced pressure, diluted with DCM, washed with water, 10% NaHCO$_3$ aq. solution, dried over anhyd. MgSO$_4$. The solvent was concentrated under reduced pressure, purified by column chromatography (10% diethyl ether in hexane) to afford 71 mg of the title compound as a pale yellow oil (57% yield). $^1$H NMR (δ, 23° C., CDCl$_3$): 4.28 (q, J=7.1 Hz, 2H), 2.44 (s, 3H), 1.98 (s, 3H), 1.31 (t, J=7.1 Hz, 3H).

C-3. Oxidative Olefin Functionalization

Synthesis of 1-phenylethane-1,2-diyl diacetate

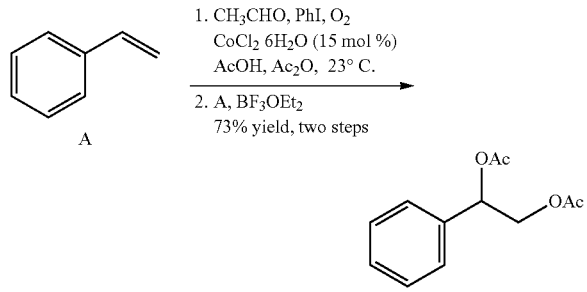

A-20 mL vial was charged with AcOH (0.9 mL), Ac2O (0.1 mL), iodobenzene (41.0 mg, 0.201 mmol, 1.00 eq.) and CoCl$_2$.6H$_2$O (3.9 mg, 30.0 μmol, 15 mol %) and stoppered with a septum. The reaction vial was purged with O$_2$ for 5 min and then acetaldehyde (34 μL, 0.608 mmol, 3.00 eq.) was added to the reaction mixture. The reaction mixture was stirred for 3 h at ambient temperature under 1 atm O$_2$ (supplied via a balloon). Styrene (26.0 μL, 0.201 mmol, 1.00 eq.) and 0.202 M BF$_3$.OEt$_2$ solution in AcOH (100 μL, 20.2 μmol, 10 mol %) were added and stirred at room temperature for 6 hours. Saturate aqueous NaHCO$_3$ and CH$_2$Cl$_2$ were added to the reaction mixture and the aqueous layer was extracted with CH$_2$Cl$_2$ (2×3 mL). Purification by SiO$_2$ chromatography using a hexane/EtOAc (9/1, v/v) eluent afforded 38.8 mg of the title compound (73% yield). $^1$H NMR (300 MHz, δ, 23° C., CDCl$_3$): 7.43-7.30 (m, 5H), 6.03-6.00 (m, 1H), 4.33-4.29 (m, 2H), 2.12 (s, 3H), 2.06 (s, 3H) ppm. $^{13}$C-NMR (75 MHz, δ, 23° C., CDCl$_3$): 170.1, 170.0, 136.5, 128.7, 128.7, 126.7, 73.3, 66.1, 21.1, 20.8 ppm. The recorded spectra are in good agreement with reported data.

Synthesis of 1-(4-fluorophenyl)ethane-1,2-diyl diacetate (20)

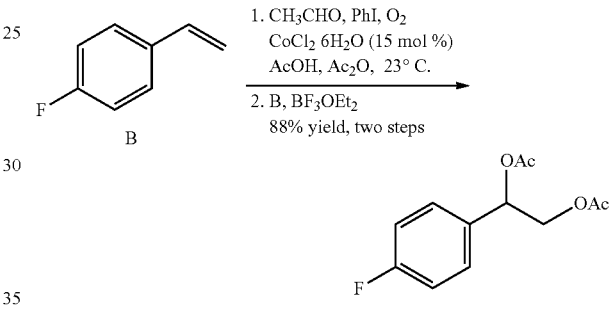

A-20 mL vial was charged with AcOH (0.9 mL), Ac2O (0.1 mL), iodobenzene (61.0 mg, 0.299 mmol, 1.50 eq.) and CoCl$_2$.6H$_2$O (0.5 mg, 3.85 μmol, 2 mol %) and stoppered with a septum. The reaction vial was purged with O$_2$ for 5 min and then acetaldehyde (168 μL, 3.00 mmol, 15.0 eq.) was added to the reaction mixture. The reaction mixture was stirred for 6 hours at ambient temperature under 1 atm O$_2$ (supplied via a balloon). 4-Fluorostyrene (24.0 μL, 0.201 mmol, 1.00 eq.) and 0.202 M BF$_3$.OEt$_2$ solution in AcOH (100 μL, 20.2 μmol, 10 mol %) were added and stirred at room temperature for 6 hours. Saturate aqueous NaHCO$_3$ and CH$_2$Cl$_2$ were added to the reaction mixture and the aqueous layer was extracted with CH$_2$Cl$_2$ (2×3 mL). The solvent was concentrated under reduced pressure and purified by column chromatography on SiO$_2$ using a hexane/EtOAc (9/1, v/v) eluent to afford 42.4 mg of the title compound (88% yield). $^1$H-NMR (300 MHz, δ, 23° C., CDCl$_3$): 7.37-7.32 (m, 2H), 7.05-7.02 (t, 2H), 4.30-4.27 (m, 2H), 2.11 (s, 3H), 2.05 (s, 3H) ppm. $^{13}$C-NMR (75 MHz, δ, 23° C., CDCl$_3$): 170.5, 169.9, 162.7 (d, J=274.2 Hz), 132.4 (d, J=3.3 Hz), 128.6 (d, J=8.3 Hz), 115.6 (d, J=21.5 Hz), 72.6, 65.9, 21.1, 20.7 ppm. $^{19}$F-NMR (500 MHz, δ, 23° C., CDCl$_3$): −112.9 ppm (C$_6$H$_5$F was used as a standard, −113.1 ppm). The recorded spectra are in good agreement with reported data.

D. Supporting Data

Optimization of Aerobic Oxidation of Iodobenzene

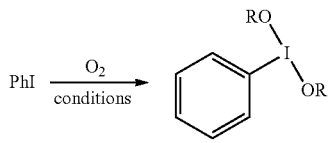

Representative Procedure. A 20-mL scintillation vial was charged with DCE (2 mL), iodobenzene (84 mg, 0.411 mmol, 1.00 eq.) and $CoCl_2.6H_2O$ (0.9 mg, 0.004 mmol, 1 mol %) and was fitted with a rubber septum. The reaction vessel was purged with $O_2$ for 5 min before acetaldehyde (224 μL, 4.068 mmol, 10.00 eq.) was added in one portion. The reaction mixture was stirred under 1 atm $O_2$, delivered by inflated balloon, at 23° C., for 16 h. Solvent was removed in vacuo and the crude residue was analyzed by $^1H$ NMR.

Evaluation of Aerobic Oxidation of Iodobenzene in the Absence of Radical Initiator

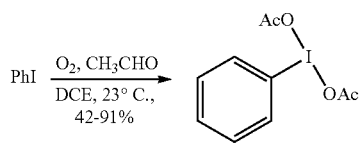

A 20-mL scintillation vial was charged with DCE (2 mL) and iodobenzene (84 mg, 0.411 mmol, 1.00 eq.) and was fitted with a rubber septum. The reaction vessel was purged with $O_2$ for 5 min before acetaldehyde (224 μL, 4.068 mmol, 10.00 eq.) was added in one portion. The reaction mixture was stirred under 1 atm $O_2$, delivered by inflated balloon, at 23° C., for 16 h. Removal of the solvent in vacuo afforded the title compound (41-91% yield). $^1H$-NMR (δ, 23° C., $CDCl_3$): 8.09 (d, J=7.3 Hz, 2H), 7.63-7.47 (m, 3H), 2.01 (s, 6H).

Evaluation of Aerobic Oxidation of Iodobenzene in the Presence of BHT

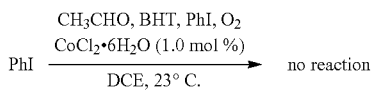

A 20-mL scintillation vial was charged with DCE (2 mL), iodobenzene (84 mg, 0.411 mmol, 1.00 eq.), BHT (89 mg, 4.039 mmol, 10.00 eq.) and $CoCl_2.6H_2O$ (0.9 mg, 0.004 mmol, 1 mol %) and was fitted with a rubber septum. The reaction vessel was purged with $O_2$ for 5 min before acetaldehyde (224 μL, 4.068 mmol, 10.00 eq.) was added in one portion. The reaction mixture was stirred under 1 atm $O_2$, delivered by inflated balloon, at 23° C., for 16 h. Removal of the solvent in vacuo didn't afford iodobenzene diacetate, instead we got back iodobenzene and BHT, identified from crude $^1H$ NMR.

E. Kinetics Experiments

Measurement of Aerobic Oxidation Kinetics in $CDCl_3$

A 20-mL scintillation vial was charged with $CDCl_3$ (4 mL), iodobenzene (163.2 mg, 0.800 mmol, 1.00 eq.) and $CoCl_2.6H_2O$ (1.0 mg, 7.70 μmol, 1 mol %) and stoppered with a rubber septum. The reaction vessel was purged with $O_2$ for 5 min. An aliquot (0.200 mL) was removed and the 1H-NMR spectrum was recorded. Acetaldehyde (450 μL, 8.04 mmol, 10.1 eq.) was added to the reaction vessel and the reaction mixture was stirred at 23° C. under 1 atm $O_2$, delivered by inflated balloon. Aliquots (0.200 mL) were removed periodically for $^1H$ NMR analysis. Monitoring was continued until the reaction had reached completion, as evidenced by the disappearance of 1H NMR resonances attributable to iodobenzene.

Measurement of Aerobic Oxidation Kinetics in $CDCl_3$ with No Added Initiator A 20-mL scintillation vial was charged with $CDCl_3$ (4 mL), iodobenzene (163.2 mg, 0.800 mmol, 1.00 eq.) and stoppered with a rubber septum. The reaction vessel was purged with O2 for 5 min. An aliquot (0.200 mL) was removed and the 1H-NMR spectrum was recorded. Acetaldehyde (450 μL, 8.04 mmol, 10.1 eq.) was added to the reaction vessel and the reaction mixture was stirred at 23° C. under 1 atm $O_2$, delivered by inflated balloon. Aliquots (0.200 mL) were removed periodically for $^1H$ NMR analysis. Monitoring was continued until the reaction had reached completion, as evidenced by the disappearance of $^1H$ NMR resonances attributable to iodobenzene.

Kinetics Measurement in $d_4$-Acetic Acid

A 20-mL scintillation vial was charged with deuterated acetic acid-$d_4$ (4 mL), iodobenzene (163.2 mg, 0.800 mmol, 1.00 eq.), and $CoCl_2.6H_2O$ (1.0 mg, 7.70 μmol, 1 mol %) and stoppered with a rubber septum. Mesitylene (50 μL, 0.359 mmol) was added to the reaction mixture as internal standard. The reaction vessel was purged with $O_2$ for 5 min, and an aliquot (0.200 mL) was removed and 1H-NMR spectroscopy was recorded. Acetaldehyde (450 μL, 8.04 mmol, 10.1 eq.) was added to the reaction vessel and the reaction mixture was stirred at 23° C. under 1 atm $O_2$, delivered by inflated balloon. Monitoring was continued until the reaction had reached completion, as evidenced by the disappearance of $^1H$ NMR resonances attributable to iodobenzene.

Kinetics Measurement in $d_4$-Acetic Acid in the Absence of Radical Initiator A 20-mL scintillation vial was charged with deuterated acetic acid-$d_4$ (4 mL), iodobenzene (163.2 mg, 0.800 mmol, 1.00 eq.) and stoppered with a rubber septum. Mesitylene (50 μL, 0.359 mmol) was added to the reaction mixture as internal standard. The reaction vessel was purged with $O_2$ for 5 min, and an aliquot (0.200 mL) was removed and $^1H$-NMR spectroscopy was recorded. Acetaldehyde (450 μL, 8.04 mmol, 10.1 eq.) was added to the reaction vessel and the reaction mixture was stirred at 23° C. under 1 atm $O_2$, delivered by inflated balloon. Monitoring was continued up to 10 h.

Mass Spectrometry Data

Sample Preparation in Experimental Condition

A 20-mL scintillation vial was charged with $CHCl_3$ (1.50 mL), iodobenzene (41.0 mg, 0.201 mmol, 1.00 eq.) and $CoCl_2 \cdot 6H_2O$ (0.3 mg, 2.31 μmol, 1 mol %) and stoppered with a rubber septum. The reaction vessel was purged with $O_2$ for 5 min. Acetaldehyde (115 μL, 2.06 mmol, 10.2 eq.) was added to the reaction vessel and the reaction mixture was stirred at 23° C. under 1 atm $O_2$, delivered by inflated balloon, for 1.5 h which the compound E was in the maximum concentration determined by kinetics measurement. ESI HRMS m/z $(M+Na)^+$ calcd. 143.03148, obsd. 143.08181.

Sample Preparation without Iodobenzene

A 20-mL scintillation vial was charged with $CHCl_3$ (1.50 mL) and $CoCl_2 \cdot 6H_2O$ (0.3 mg, 2.31 μmol, 1 mol %) and stoppered with a rubber septum. The reaction vessel was purged with $O_2$ for 5 min. Acetaldehyde (115 μL, 2.06 mmol, 10.2 eq.) was added to the reaction vessel and the reaction mixture was stirred at 23° C. under 1 atm $O_2$, delivered by inflated balloon, for 1.5 h which 1-hydroxyethyl ethaneperoxoate (E) was in the maximum concentration determined by kinetics measurement. ESI HRMS m/z $(M+Na)+$ calcd. 143.03148, obsd. 143.08182.

The invention claimed is:

1. A method of synthesis of an aryl hypervalent iodine reagent, comprising contacting an aryl iodide in a suitable solvent with an aliphatic aldehyde and a source of dioxygen, thereby forming the aryl hypervalent iodine reagent,
wherein the aryl iodide is an optionally substituted phenyl iodide and the aliphatic aldehyde has the formula RCHO, wherein R is a $C_1$-$C_6$ alkyl.

2. The method of claim 1, wherein the aryl hypervalent iodine reagent is an aryl iodine I(III) or I(V) reagent.

3. The method of claim 1, wherein the aryl hypervalent iodine reagent has the structure of Formula (I), Formula (II), or Formula (III):

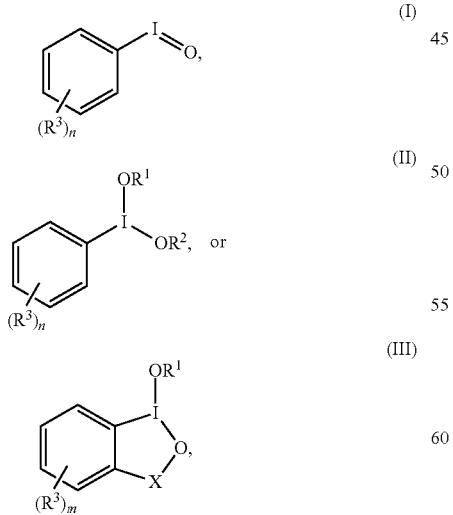

wherein:
$R^1$ is H, Ts, or Ac;
$R^2$ is H, optionally substituted $C_1$-$C_6$ alkyl, Ac, or Ts;
$R^3$, independently at each occasion, is H, optionally substituted $C_1$-$C_6$ alkyl, optionally substituted $C_1$-$C_6$ alkoxy, COOH, Cl, Br, $CF_3$, $NO_2$, $SO_2R^4$, optionally substituted aryl, or optionally substituted heteroaryl, or two $R^3$ at adjacent carbon atoms together with the atoms at which they are attached form an optionally substituted 5 or 6-membered aliphatic or aromatic cycle;
$R^4$ is optionally substituted $C_1$-$C_6$ alkyl, optionally substituted aryl, or optionally substituted heteroaryl;
X is C(O), $C(CH_3)_2$, $C(CF_3)_2$, or I(OAc);
n is 0, 1, 2, 3, 4, or 5; and
m is 0, 1, 2, 3, or 4.

4. The method of claim 1, wherein the aryl hypervalent iodine reagent has the structure of Formulae 1a, 1b, 1c, 1d, 1e, 1f, 1g, 2a, 2b, 2c, 2d, 2d, 2e, 2f, 2g, 3, 4, 5, 6, or 7:

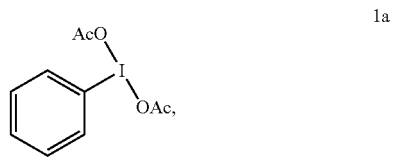

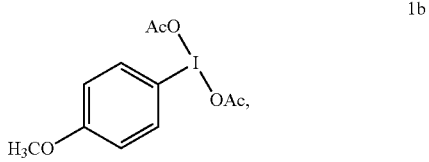

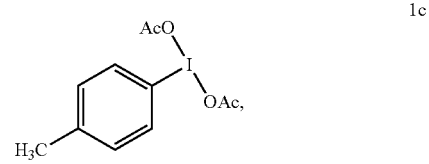

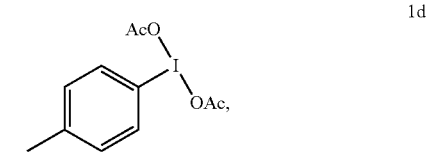

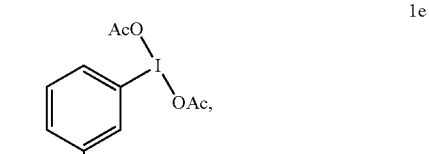

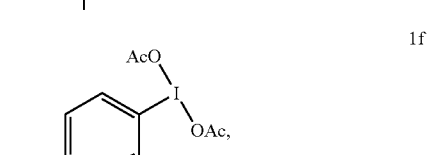

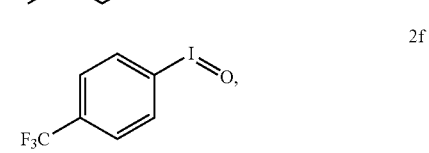

-continued

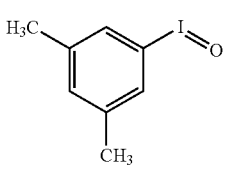
2g

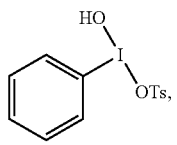
3

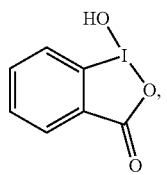
4

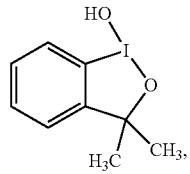
5

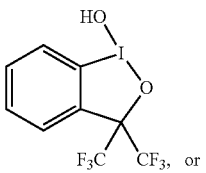
6

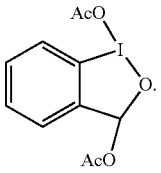
7

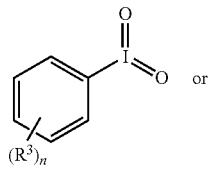

5. The method of claim 1, wherein the aryl hypervalent iodine reagent has the structure of Formula (IV) or Formula (V):

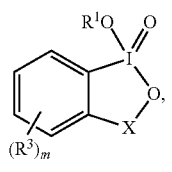

wherein:
R$^1$ is H, Ts, or Ac;
R$^3$, independently at each occasion, is H, optionally substituted C$_1$-C$_6$ alkyl, optionally substituted C$_1$-C$_6$ alkoxy, COOH, Cl, Br, CF$_3$, NO$_2$, SO$_2$R$^4$, optionally substituted aryl, or optionally substituted heteroaryl, or two R$^3$ at adjacent carbon atoms together with the atoms at which they are attached form an optionally substituted 5 or 6-membered aliphatic or aromatic cycle;
R$^4$ is optionally substituted C$_1$-C$_6$ alkyl, optionally substituted aryl, or optionally substituted heteroaryl;
X is C(O), C(CH$_3$)$_2$, C(CF$_3$)$_2$, or I(OAc);
n is 0, 1, 2, 3, 4, or 5; and
m is 0, 1, 2, 3, or 4.

6. The method of claim 1, wherein the aryl hypervalent iodine reagent has the structure of Formulae 21, 22, 24, 25, 26, 27, 28, 29, 30, or 31:

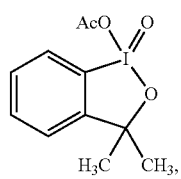
21

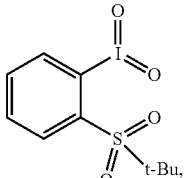
22

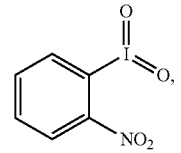
24

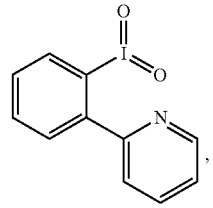
25

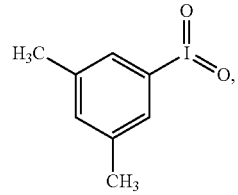
26

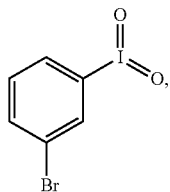
27

-continued

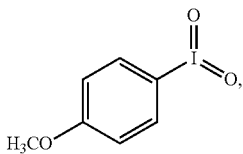

28

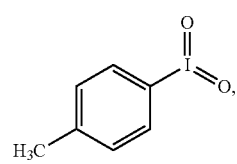

29

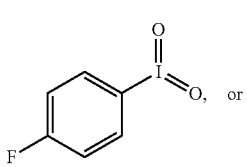

30

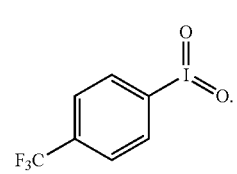

31

7. The method of claim 1, wherein the aryl iodide is an optionally substituted phenyl iodide of Formula (VI):

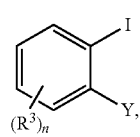

(VI)

wherein:
Y is $NO_2$, 2-pyridyl, or $SO_2$(t-Bu);
$R^3$, independently at each occasion, is H, optionally substituted $C_1$-$C_6$ alkyl, optionally substituted $C_1$-$C_6$ alkoxy, COOH, Cl, Br, $CF_3$, $NO_2$, $SO_2R^4$, optionally substituted aryl, or optionally substituted heteroaryl, or two $R^3$ at adjacent carbon atoms together with the atoms at which they are attached form an optionally substituted 5 or 6-membered aliphatic or aromatic cycle;
$R^4$ is optionally substituted $C_1$-$C_6$ alkyl, optionally substituted aryl, or optionally substituted heteroaryl; and
n is 0, 1, 2, 3, or 4.

8. The method of claim 1, wherein the aliphatic aldehyde is acetaldehyde, propionaldehyde, or butyraldehyde.

9. The method of claim 1, wherein the suitable solvent is a coordinating solvent, a non-coordinating solvent, or a protic solvent.

10. The method of claim 9, wherein the suitable solvent is 1,2-dichloroethane, nitromethane, acetic acid, or acetonitrile.

11. The method of claim 1, wherein the contacting is performed in the presence of an autooxidation initiator.

12. The method of claim 11, wherein the autooxidation initiator is $CoCl_2.6H_2O$, $Cu(OAc)_2.H_2O$, or $Mn(OAc)_2.4H_2O$.

13. The method of claim 1, wherein the source of dioxygen is air or dioxygen gas.

14. The method of claim 1, wherein the method is performed at atmospheric pressure.

15. The method of claim 1, wherein the method is performed at a temperature between about 20° C. and about 30° C.

16. A method of oxidizing an organic compound, the method comprising contacting an organic compound in a suitable solvent with an optionally substituted phenyl iodide, an aliphatic aldehyde of the formula RCHO, wherein R is a $C_1$-$C_6$ alkyl, and dioxygen, wherein the organic compound is a primary alcohol, a secondary alcohol, a diol, a ketone, or an olefin.

17. The method of claim 16, wherein the suitable solvent is 1,2-dichloroethane.

18. The method of claim 16, wherein the contacting is done in the presence of a catalytic amount of an autooxidation initiator, wherein the autooxidation initiator is $CoCl_2.6H_2O$, $Cu(OAc)_2.H_2O$, $Mn(OAc)_2.4H_2O$, or a combination thereof.

19. The method of claim 16, wherein the method is performed in the presence of p-TsOH or [TBA]Br.

20. The method of claim 16, wherein the optionally substituted phenyl iodide is present in a less than stoichiometric amount relative to the organic compound.

21. The method of claim 16, wherein the optionally substituted phenyl iodide is present in a catalytic amount.

22. The method of claim 16, wherein the source of dioxygen is air or dioxygen gas.

23. The method of claim 1, wherein the optionally substituted phenyl iodide is iodobenzene, 2-iodonitrobenzene, 2-iodobenzoic acid, 4-iodoanisole, 4-iodotoluene, 4-fluoroiodobenzene, 4-trifluoromethyliodobenzene, 3-bromoiodobenzene, 2,5-dimethyliodobenzene, 4-trifluoromethyl-iodobenzene, 2-(2-iodophenyl)propan-2-ol, 1,1,1,3,3,3-hexafluoro-2-(2-iodophenyl)propan-2-ol, 1,2-diiodobenzene, 1-(tert-butylsulfonyl)-2-iodobenzene, 2-(2-iodophenyl)pyridine, or 1,2-diiodobenzene.

24. The method of claim 16, wherein the optionally substituted phenyl iodide is a phenyl iodide of Formula (VI):

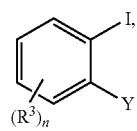

(VI)

wherein:
Y is $NO_2$, 2-pyridyl, or $SO_2$(t-Bu);
$R^3$, independently at each occasion, is H, optionally substituted $C_1$-$C_6$ alkyl, optionally substituted $C_1$-$C_6$ alkoxy, COOH, Cl, Br, $CF_3$, $NO_2$, $SO_2R^4$, optionally substituted aryl, or optionally substituted heteroaryl, or two $R^3$ at adjacent carbon atoms together with the atoms at which they are attached form an optionally substituted 5 or 6-membered aliphatic or aromatic cycle;
$R^4$ is optionally substituted $C_1$-$C_6$ alkyl, optionally substituted aryl, or optionally substituted heteroaryl; and
n is 0, 1, 2, 3, or 4.

25. The method of claim 16, wherein the optionally substituted phenyl iodide is iodobenzene, 2-iodonitrobenzene, 2-iodobenzoic acid, 4-iodoanisole, 4-iodotoluene, 4-fluoroiodobenzene, 4-trifluoromethyliodobenzene, 3-bromoiodobenzene, 2,5-dimethyliodobenzene, 4-trifluoromethyl-iodobenzene, 2-(2-iodophenyl)propan-2-ol, 1,2-diiodobenzene, 1-(tert-butylsulfonyl)-2-iodobenzene, 1,1,1,3,3,3-hexafluoro-2-(2-iodophenyl)propan-2-ol, 2-(2-iodophenyl)pyridine, or 1,2-diiodobenzene.

\* \* \* \* \*